(12) United States Patent
Lawrence et al.

(10) Patent No.: US 12,350,321 B2
(45) Date of Patent: *Jul. 8, 2025

(54) FIBROIN-DERIVED PROTEIN COMPOSITION

(71) Applicant: SILK TECHNOLOGIES, LTD., Plymouth, MN (US)

(72) Inventors: Brian D. Lawrence, Plymouth, MN (US); David W. Infanger, Plymouth, MN (US)

(73) Assignee: SILK TECHNOLOGIES, LTD., Plymouth, MN (US)

(*) Notice: Subject to any disclaimer, the term of this patent is extended or adjusted under 35 U.S.C. 154(b) by 0 days.

This patent is subject to a terminal disclaimer.

(21) Appl. No.: 18/431,596

(22) Filed: Feb. 2, 2024

(65) Prior Publication Data

US 2024/0216478 A1 Jul. 4, 2024

Related U.S. Application Data

(60) Division of application No. 17/360,674, filed on Jun. 28, 2021, now Pat. No. 11,890,328, which is a continuation of application No. 16/680,186, filed on Nov. 11, 2019, now Pat. No. 11,045,524, which is a continuation of application No. 15/912,295, filed on Mar. 5, 2018, now Pat. No. 10,471,128, which is a continuation of application No. 15/212,086, filed on Jul. 15, 2016, now Pat. No. 9,907,836, which is a continuation of application No. 14/831,473, filed on Aug. 20, 2015, now Pat. No. 9,394,355.

(60) Provisional application No. 62/193,790, filed on Jul. 17, 2015, provisional application No. 62/039,675, filed on Aug. 20, 2014.

(51) Int. Cl.
| | |
|---|---|
| A61K 38/39 | (2006.01) |
| A23J 3/00 | (2006.01) |
| A23L 2/66 | (2006.01) |
| A23L 33/17 | (2016.01) |
| A61K 35/64 | (2015.01) |
| A61K 45/06 | (2006.01) |
| C07K 14/78 | (2006.01) |

(52) U.S. Cl.
CPC .......... *A61K 38/39* (2013.01); *A23J 3/00* (2013.01); *A23L 2/66* (2013.01); *A23L 33/17* (2016.08); *A61K 35/64* (2013.01); *A61K 45/06* (2013.01); *C07K 14/78* (2013.01); *A23V 2002/00* (2013.01)

(58) Field of Classification Search
None
See application file for complete search history.

(56) References Cited

U.S. PATENT DOCUMENTS

| | | | |
|---|---|---|---|
| 5,591,426 A | 1/1997 | Dabrowski et al. | |
| 5,895,645 A | 4/1999 | Dabrowski et al. | |
| 6,034,220 A | 3/2000 | Stedronsky | |
| 6,280,747 B1 | 8/2001 | Philippe et al. | |
| 7,060,260 B2 | 6/2006 | Fahnestock et al. | |
| 7,115,388 B2 | 10/2006 | Tsubouchi | |
| 7,193,038 B2 | 3/2007 | Tsubouchi et al. | |
| 7,635,755 B2 | 12/2009 | Kaplan et al. | |
| 8,097,583 B2 | 1/2012 | Scheibel et al. | |
| 8,361,617 B2 | 1/2013 | Kaplan et al. | |
| 8,420,077 B2 | 4/2013 | Altman et al. | |
| 8,481,681 B2 | 7/2013 | Sutherland et al. | |
| 8,496,976 B2 | 7/2013 | Gore et al. | |
| 8,614,293 B2 | 12/2013 | Kaplan et al. | |
| 8,742,069 B2 | 6/2014 | Kaplan et al. | |
| 9,394,355 B2 * | 7/2016 | Lawrence | A23J 3/00 |
| 9,907,836 B2 * | 3/2018 | Lawrence | A61K 35/64 |
| 10,471,128 B2 * | 11/2019 | Lawrence | A61K 35/64 |
| 11,045,524 B2 * | 6/2021 | Lawrence | A61K 38/39 |
| 11,242,367 B2 | 2/2022 | Lawrence et al. | |
| 2003/0206897 A1 | 11/2003 | O'prey et al. | |
| 2004/0097709 A1 | 5/2004 | Armato et al. | |
| 2004/0219630 A1 | 11/2004 | Tsubouchi | |
| 2004/0265260 A1 | 12/2004 | Tsubouchi et al. | |
| 2005/0143296 A1 | 6/2005 | Tsubouchi et al. | |
| 2005/0196370 A1 | 9/2005 | Yu et al. | |
| 2005/0202097 A1 | 9/2005 | Maskin | |
| 2006/0106104 A1 | 5/2006 | Vehige et al. | |

(Continued)

FOREIGN PATENT DOCUMENTS

| | | |
|---|---|---|
| CN | 101194666 A | 6/2008 |
| CN | 102860969 A | 1/2013 |

(Continued)

OTHER PUBLICATIONS

Applegate et al., "Photocrosslinking of Silk Fibroin Using Riboflavin for Ocular Prostheses," Adv Mater., 28 (12):2417-2420, Mar. 2016.
Asakura et al., "Possible Implications of Serine and Tyrosine Residues and Intermolecular Interactions on the Appearance of Silk I Structure of Bombyx Mori Silk Fibroin-Derived Synthetic Peptides: High-Resolution 13C Cross-Polarization/Magic-Angle Spinning NMR Study," Biomacromolecules, 6(1):468-474, Jan.-Feb. 2005.
Chon et al., "Silk Fibroin Hydrolysate Inhibits Osteoclastogenesis and Induces Apoptosis of Osteoclasts Derived from RAW 264.7 Cells," Int J Mol Med., 30(5):1203-1210, Nov. 2012.

(Continued)

*Primary Examiner* — Christina Bradley
(74) *Attorney, Agent, or Firm* — Haukaas Fortius PLLC; Michael Haukaas

(57) ABSTRACT

A protein composition derived from silk fibroin, which composition possesses enhanced solubility and stability in aqueous solutions. The primary amino acid sequence of native fibroin is modified in the SDP such that cysteine disulfide bonds between the fibroin heavy and fibroin light protein chains are reduced or eliminated. Additionally, the composition can have a serine content that is reduced by greater than 40% compared to native fibroin protein, and the average molecular weight of the SDP is less than about 100 kDa.

9 Claims, 9 Drawing Sheets

Specification includes a Sequence Listing.

(56) References Cited

U.S. PATENT DOCUMENTS

| | | |
|---|---|---|
| 2008/0219938 A1 | 9/2008 | Grune |
| 2009/0234026 A1 | 9/2009 | Kaplan et al. |
| 2011/0008406 A1 | 1/2011 | Altman et al. |
| 2011/0105402 A1 | 5/2011 | Kim et al. |
| 2011/0288273 A1 | 11/2011 | Yang et al. |
| 2012/0040907 A1 | 2/2012 | DiBenedetto et al. |
| 2012/0052124 A1 | 3/2012 | Kaplan et al. |
| 2012/0171256 A1 | 7/2012 | Zhang et al. |
| 2013/0039986 A1 | 2/2013 | Kaplan et al. |
| 2013/0060008 A1 | 3/2013 | Wang et al. |
| 2013/0158131 A1 | 6/2013 | Kaplan et al. |
| 2013/0165004 A1 | 6/2013 | Kaplan et al. |
| 2013/0190222 A1 | 7/2013 | Kaplan et al. |
| 2013/0243693 A1 | 9/2013 | Omenetto et al. |
| 2013/0243709 A1 | 9/2013 | Hanson et al. |
| 2014/0193466 A1 | 7/2014 | Lawrence et al. |
| 2014/0235554 A1 | 8/2014 | Lawrence et al. |
| 2015/0093340 A1 | 4/2015 | Altman et al. |
| 2016/0096878 A1 | 4/2016 | Lawrence et al. |

FOREIGN PATENT DOCUMENTS

| | | |
|---|---|---|
| CN | 103239707 A | 8/2013 |
| CN | 103225126 B | 10/2014 |
| JP | S55124793 A | 9/1980 |
| JP | H02277885 A | 11/1990 |
| JP | 0767686 A | 3/1995 |
| JP | H08295697 A | 11/1996 |
| JP | 2000143472 A | 5/2000 |
| WO | 1999033899 A1 | 7/1999 |
| WO | 2007130364 A2 | 11/2007 |
| WO | 2009088119 A1 | 7/2009 |
| WO | 2012170655 A1 | 12/2012 |
| WO | 2013126799 A1 | 8/2013 |
| WO | 2013159101 A1 | 10/2013 |
| WO | 2014145002 A2 | 9/2014 |
| WO | 2014145002 A3 | 9/2014 |
| WO | 2014152097 A1 | 9/2014 |
| WO | 2015077300 A1 | 5/2015 |
| WO | 2016100721 A1 | 6/2016 |

OTHER PUBLICATIONS

Collin et al., "Molecular Evolution of Lepidopteran Silk Proteins: Insights from the Ghost Moth, Hepialus californicus," J Mol Evol., 70:519-529; May 2010.

Daithankar et al., "Moisturizing Efficiency of Silk Protein Hydrolysate: Silk Fibroin," Indian J. Biotech., 4:115-121: Jan. 4, 2005.

Extended Search Report of the European Patent Office dated Apr. 24, 2018 in EP Application No. 15833824.4.6 (EP3182985A1), 7pgs.

Greving et al., "Shear-Induced Self-Assembly of Native Silk Proteins into Fibrils Studied by Atomic Force Microscopy," Biomacromolecules, 13(3):676-682, Feb. 21, 2012.

Hardy et al., "Polymeric Materials Based on Silk Proteins," Polymer, 49(20):4309-4327, Sep. 2008.

Harkin et al., "Silk Fibroin in Ocular Tissue Reconstruction," Biomaterials, 32(10):2445-58, Apr. 2011.

Hashimoto et al., "Quantitative Evaluation of Fibroblast Migration on a Silk Fibroin Surface and TGFBI Gene Expression," J Biomater Sci Polym Ed., 24(2):158-169, Jan. 2013.

International Search Report and Written Opinion of the ISA/US dated Dec. 14, 2015 in International Application No. PCT/US2015/046141; 17pgs.

International Search Report and Written Opinion of the ISA/US dated Dec. 22, 2017 in International Application No. PCT/US2017/026656; 12pgs.

International Search Report and Written Opinion of the ISA/US dated Dec. 4, 2017 in International Application No. PCT/US2017/046659; 11pgs.

Kang et al., "Preparation and Characterization of Low Molecular Weight Silk Fibroin by High-Temperature and High-Pressure Method," J. Applied Polymer Sci., 85(14):2890-2895, Sep. 2002.

Kaur et al., "Photoprotection by Silk Cocoons," Biomacromolecules, 14(10):3660-3667, Sep. 3, 2013.

Kim et al., "A Transparent Artificial Dura Mater Made of Silk Fibroin as an Inhibitor of Inflammation in Craniotomized Rats," J Neurosurg., 114(2):485-490, Feb. 2011.

Lawrence et al., "Silk Film Culture System for in vitro Analysis and Biomaterial Design," J Vis Exp., 62:1-6, Apr. 2012.

Matsumoto et al., "Mechanisms of Silk Fibroin Sol-Gel Transitions," J Phys Chem B., 110(43):21630-2638, Nov. 2, 2008.

Patchornik et al., "Nonenzymatic Cleavages of Peptide Chains at the Cysteine and Serine Residues Through Their Conversion Into Dehydroalanine. I. Hydrolytic and Oxidative Cleavage of Dehydroalanine Residues," J. Am. Chem. Soc., 86(6):1206-1212, Mar. 20, 1964.

Rockwood et al., "Materials Fabrication from Bombyx mori Silk Fibroin," Nat Protoc., 6(10):1612-1631, Sep. 2011.

Siritientong et al., "The effects of Bombyx mori silk strain and extraction time on the molecular and biological characteristics of sericin," Bioscience, Biotechnology, and Biochemistry., vol. 80, No. 2, 241-249; Aug. 2015.

Teng et al., "Physical Crosslinking Modulates Sustained Drug Release from Recombinant Silk-Elastinlike Protein Polymer for Ophthalmic Applications," J. Control Release, 156(2):186-197, Dec. 2011.

Wang et al., "Sonication-Induced Gelation of Silk Fibroin for Cell Encapsulation," Biomaterials, 29(8):1054-1064, Apr. 2008.

Wu et al., "Impact of Sterilization Methods on the Stability of Silk Fibroin Solution," Adv Mater Res., 311-313:1755-1759, Aug. 2011.

Yamada et al., "Preparation of Undegraded Native Molecular Fibroin Solution from Silkworm Cocoons," Mater Sci Eng.: C, 14(1-2):41-46, Aug. 2001.

Zhao et al., "The Effects of Different Sterilization Methods on Silk Fibroin," J Biomed Sci Eng., 4:397-402, May 2011.

* cited by examiner

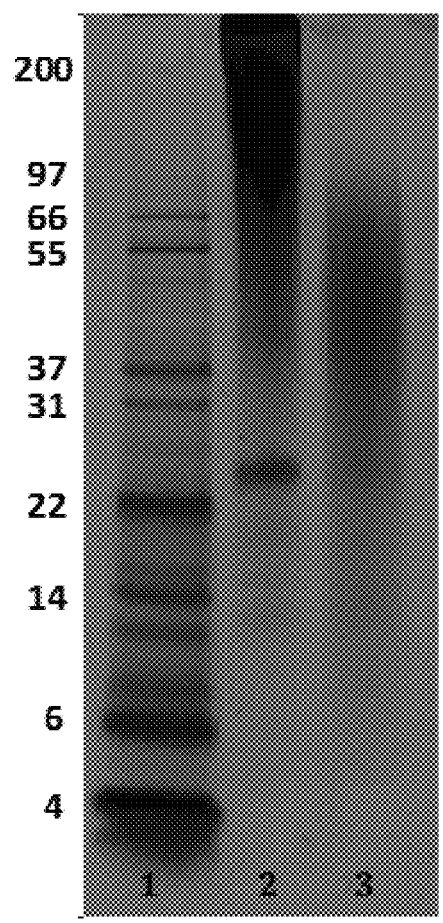
Fig. 3
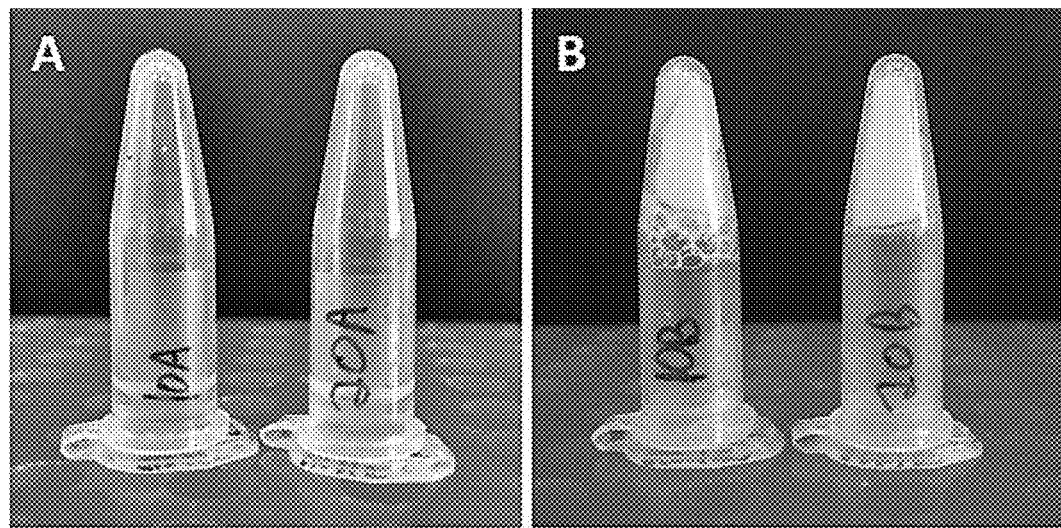
Fig. 4A-B

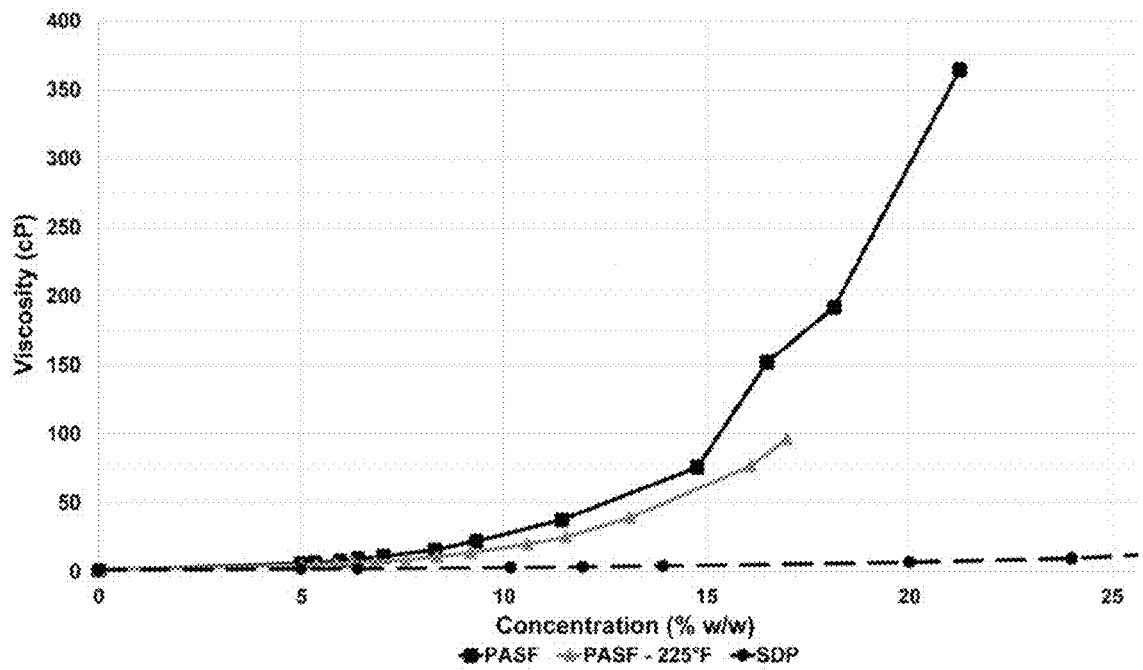
Fig. 5
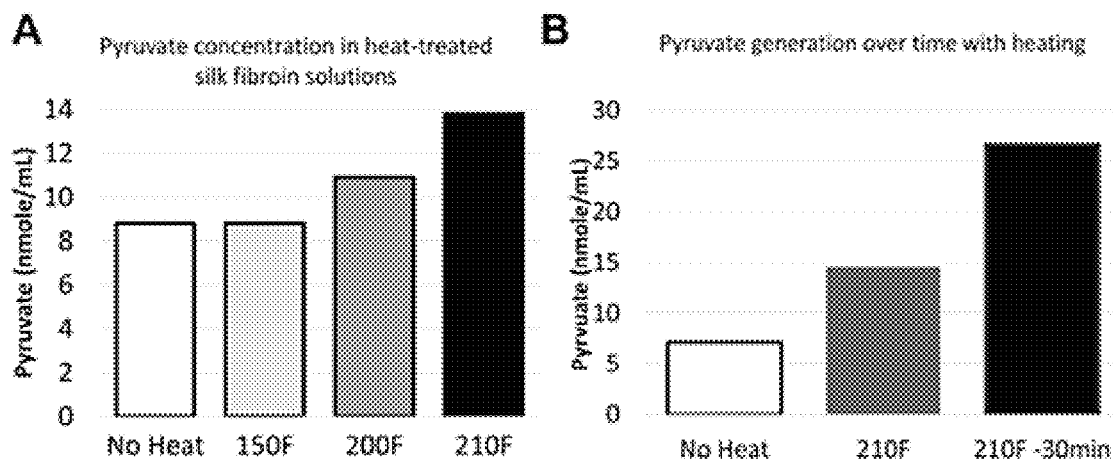
Fig. 6A-B

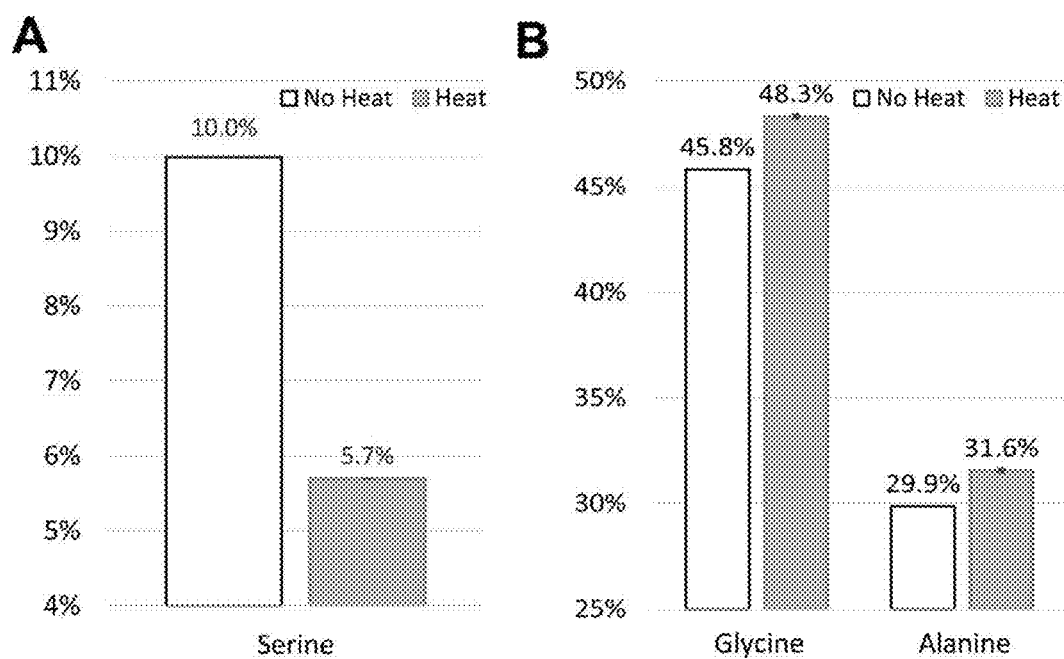
Fig. 7A-B

Fig. 9A-C

SEQUENCE LISTING

```
Sequence total quantity: 1
SEQ ID NO: 1            moltype = AA  length = 4
FEATURE                 Location/Qualifiers
REGION                  1..4
                        note = Description of Artificial Sequence: Synthetic peptide
source                  1..4
                        mol_type = protein
                        organism = synthetic construct
SEQUENCE: 1
GAGA                                                                    4
```

FIBROIN-DERIVED PROTEIN COMPOSITION

RELATED APPLICATIONS

This application is a divisional of U.S. patent application Ser. No. 17/360,674 filed Jun. 28, 2021, which issued as U.S. Pat. No. 11,890,328 on Feb. 6, 2024, which is a continuation of U.S. patent application Ser. No. 16/680,186 filed Nov. 11, 2019, which issued as U.S. Pat. No. 11,045,524 on Jun. 29, 2021 and which is a continuation of U.S. patent application Ser. No. 15/912,295 filed Mar. 5, 2018, which issued as U.S. Pat. No. 10,471,128 and which is a continuation of U.S. patent application Ser. No. 15/212,086 filed Jul. 15, 2016, which issued as U.S. Pat. No. 9,907,836 and which is a continuation of U.S. patent application Ser. No. 14/831,473 filed Aug. 20, 2015, which issued as U.S. Pat. No. 9,394,355 and which claims priority under 35 U.S.C. § 119(e) to U.S. Provisional Patent Application Nos. 62/039,675 filed Aug. 20, 2014 and 62/193,790 filed Jul. 17, 2015, which applications are incorporated herein by reference.

SEQUENCE LISTING

The instant application contains a Sequence Listing which has been submitted electronically in XML format and is hereby incorporated by reference in its entirety. Said SML copy, created on Feb. 1, 2024, is named 114.008US6_SL and is 2,339 bytes in size.

BACKGROUND OF THE INVENTION

Silk fiber and secreted proteins from the domesticated silkworm *Bombyx mori* have been used for centuries in the textile industry. The secreted proteins have more recently been used as a biomaterial for biomedical applications, including as a structural component and as a protein solution. Natively, silkworm proteins exist as an amalgam of the silk proteins fibroin and sericin, in which sericin serves as a glue-like substance that binds with fibroin and maintains the shape of the cocoon. Removal of sericin, such as through detergent-mediated extraction, or in high-heat and high-alkaline washing, results in sericin-free fibroin fibers that include heavy and light chain fibroin proteins associated through a single disulfide linkage. Conversion of these fibrils into water-soluble silk fibroin protein requires the addition of a concentrated heavy salt (e.g., 8-10M lithium bromide), which interferes with inter- and intra-molecular ionic and hydrogen bonding that would otherwise render the fibroin protein water-insoluble.

Applications of silk fibroin proteins typically require the removal of the high LiBr salt concentrations, such as through the use of dialysis, so that the salts do not interfere with proper material function in a given environment. Without these salts to compete with ionic and hydrogen bonding of the solubilized silk fibroin, silk fibroin protein solutions are relatively unstable, are vulnerable to protein aggregation, and often precipitate out of aqueous solutions. The aggregation is thought to occur through interactions between fibroin proteins, and then subsequent material gelation driven through beta-sheet secondary protein structure formation between the hydrophobic amino acid motifs of the fibroin heavy chains. Upon formation of these structures, the transition from soluble fibroin solution to insoluble fibroin gel is rapid and is largely irreversible, thereby limiting application of the solution for aqueous solution-based applications because of limited material shelf-life.

To combat the gelling propensity of aqueous fibroin, attempts have been made to minimize protein aggregation and subsequent beta-sheet formation. Lowering the fibroin concentration in solution is a colligative approach aimed to attenuate the protein-protein interactions, which precede the formation of these structures, yet may result in a fibroin solution that is too dilute for relevant protein applications. Alternatively, modifications to the aqueous solution that would impede protein aggregation and/or beta-sheet formation (e.g., solution pH, addition of stabilizing excipients) may forestall these events. However, these modifications and chemical additions can limit downstream applications by increasing biological toxicity or by introducing incompatible agents in the solution. Accordingly, what is needed is a silk-derived protein (SDP) material that is resistant to aggregation and that has a shelf-life stability profile useful across various industries.

A novel strategy to avoid the aforementioned vulnerabilities of aqueous silk fibroin is to modify the biochemical structure and qualities of the silk fibroin protein itself rather than the aqueous solution environment. Toward this end, modifications to the silk fiber extraction process and/or the conditions involved in the production of aqueous silk fibroin can impact the primary sequence of amino acids, and therefore, the chemistry responsible for protein aggregation and beta-sheet formation. As such, the development of a process for modifying silk fibroin materials could dramatically extend the stability and shelf-life of a silk solution product.

SUMMARY

The invention provides a protein composition derived from silk fibroin. The composition intrinsically possesses enhanced solubility and stability in aqueous solutions. In one embodiment, the invention provides a protein composition prepared by a process comprising heating an aqueous fibroin solution at an elevated pressure. The aqueous fibroin solution includes lithium bromide at a concentration of at least 8M. The aqueous fibroin solution is heated to at least about 105° C. (221° F.) under a pressure of at least about 10 PSI for at least about 20 minutes, to provide the protein composition. The polypeptides of the protein composition comprise less than 8.5% serine amino acid residues, and the protein composition has an aqueous viscosity of less than 5 cP as a 10% w/w solution in water.

In other embodiments, the invention provides a protein composition prepared by a process comprising heating an aqueous fibroin solution at an elevated pressure, wherein the aqueous fibroin solution comprises lithium bromide at a concentration of 9-10M, and wherein the aqueous fibroin solution is heated to a temperature in the range of about 115° C. (239° F.) to about 125° C. (257° F.), under a pressure of about 14 PSI to about 20 PSI for at least about 20 minutes; to provide the protein composition. The protein composition can include less than 6.5% serine amino acid residues and the protein composition can have an aqueous viscosity of less than 10 cP as a 15% w/w solution in water.

The invention also provides a fibroin-derived protein composition that possesses enhanced stability in aqueous solution, wherein: the primary amino acid sequences of the fibroin-derived protein composition differs from native fibroin by at least by at least 4% with respect to the combined difference in serine, glycine, and alanine content; cysteine disulfide bonds between the fibroin heavy and fibroin light protein chains are reduced or eliminated; the composition has a serine content that is reduced by greater than 25% compared to native fibroin protein; and wherein the average molecular weight of the silk derived protein is less than about 100 kDa.

In another embodiment, the invention provides a fibroin-derived protein composition that possesses enhanced stability in aqueous solution, wherein: the primary amino acid sequences of the fibroin-derived protein composition differs from native fibroin by at least by at least 6% with respect to the combined difference in serine, glycine, and alanine content; cysteine disulfide bonds between the fibroin heavy and fibroin light protein chains are reduced or eliminated; the composition has a serine content that is reduced by greater than 40% compared to native fibroin protein; and wherein the average molecular weight of the silk derived protein is less than about 96 kDa.

The invention further provides a fibroin-derived protein composition that possesses enhanced stability in aqueous solutions, wherein: the primary amino acid sequences of the fibroin-derived protein composition is modified from native silk fibroin; cysteine disulfide bonds between the fibroin heavy and fibroin light protein chains are reduced or eliminated; the average molecular weight of the silk derived protein is less than about 100 kDa; and the fibroin-derived protein composition maintains an optical absorbance at 550 nm of less than 0.25 for at least two hours after five seconds of ultrasonication.

In another embodiment, the invention provides a fibroin-derived protein composition that possesses enhanced stability in aqueous solutions, wherein: the primary amino acid sequences of the fibroin-derived protein composition is modified from native silk fibroin such that they differ from native fibroin by at least by at least 5% with respect to the combined difference in serine, glycine, and alanine content; cysteine disulfide bonds between the fibroin heavy and fibroin light protein chains are reduced or eliminated; the average molecular weight of the silk derived protein is less than about 96 kDa; and the fibroin-derived protein composition maintains an optical absorbance at 550 nm of less than 0.2 for at least two hours after five seconds of ultrasonication.

The fibroin-derived protein composition can be isolated and/or purified as a dry powder or film, for example, by dialysis and/or filtration. Alternatively, the fibroin-derived protein composition can be isolated and/or purified as a stable aqueous solution, which can be modified for use as a food or beverage composition, or as a therapeutic formulation, such as an ophthalmic formulation.

BRIEF DESCRIPTION OF THE DRAWINGS

The following drawings form part of the specification and are included to further demonstrate certain embodiments or various aspects of the invention. In some instances, embodiments of the invention can be best understood by referring to the accompanying drawings in combination with the detailed description presented herein. The description and accompanying drawings may highlight a certain specific example, or a certain aspect of the invention. However, one skilled in the art will understand that portions of the example or aspect may be used in combination with other examples or aspects of the invention.

FIG. 3. Picture of a gel showing process-mediated modification of aqueous silk fibroin protein to SDP solution. The picture shows the molecular weight (MW) distribution of an SDP Solution (Lane 3, autoclaved) versus a prior art silk fibroin solution (Lane 2, non-autoclaved). A protein standard ladder (Lane 1) and associated weights (numbers to the left of Lane 1) are provided as a reference of MW. A prominent MW band at 23-26 kDa in Lane 2 is noteworthy and is entirely absent following the autoclaving process, indicating that degradation of the fibroin light chain contributes to the enhanced stability of the SDP protein material. Also, a clear shift is observed in MW range of fibroin protein following autoclaving (Lane 3), indicating modification of the natural silk fibroin protein to the SDP material composition.

FIG. 4A-B. Images demonstrating that (A) SDP Solution material does not gel, while (B) Prior Art Silk Fibroin solution material gelled within 2 hours following ultrasonication.

FIG. 5. Impact of the fibroin processing as described herein on protein solution stability and viscosity. Summary graph illustrating solution viscosity as a function of protein concentration in Prior Art Silk Fibroin (PASF), PASF heated to 225° F. for 30 minutes (PASF-225° F.), and SDP. PASF and PASF-225° F. demonstrated a sharp increase in viscosity in solutions of >75 mg/g (7.5% w/w) and could not be concentrated higher than 200 mg/g without proteins falling out of solution. In contrast, SDP maintained a low viscosity throughout all concentrations, and was able to be concentrated to levels exceeding 240 mg/g.

FIG. 6A-B. Heat treatment of silk fibroin protein generates pyruvate, indicating modification of the fibroin primary structure. (A) Summary graph showing pyruvate concentrations in silk fibroin protein solutions (50 mg/mL) exposed to no heat, or upon heating to 65° C. (~150° F.), 90° C. (~200° F.), and 99° C. (~210° F.). (B) The duration of heat treatment further enhances pyruvate formation from silk fibroin. A 30-minute exposure of aqueous silk proteins to 99° C. (~210° F.) causes a nearly twofold increase in pyruvate levels relative to pyruvate levels at the time this temperature was initially achieved, and over fourfold that of non-heated samples.

FIG. 7A-B. Heat treatment alters the amino acid composition of native silk protein. (A) Summary graph showing serine composition as a percentage of total amino acids in fibroin protein in non-heated (i.e., 'no heat'/prior art) silk protein solution (left column, 10% serine) and SDP solution previously subject to processing as described in Example 1 (e.g., ~121° C., 17 psi) for 30 minutes ('heat'; right column, 5.7% serine). Heat treatment reduced serine composition by over 40% in SDP solution samples when compared to prior art silk fibroin solution samples. (B) Summary graph depicting percent concentrations of glycine and alanine in a prior art silk fibroin protein solution (left 'no heat' columns) and a heat and pressure processed (~121° C., 17 psi) SDP solution (right 'heat' columns). Heat and pressure processing facilitates an increase in levels of glycine and alanine relative to prior art silk fibroin solution controls.

DETAILED DESCRIPTION

Figure 1:
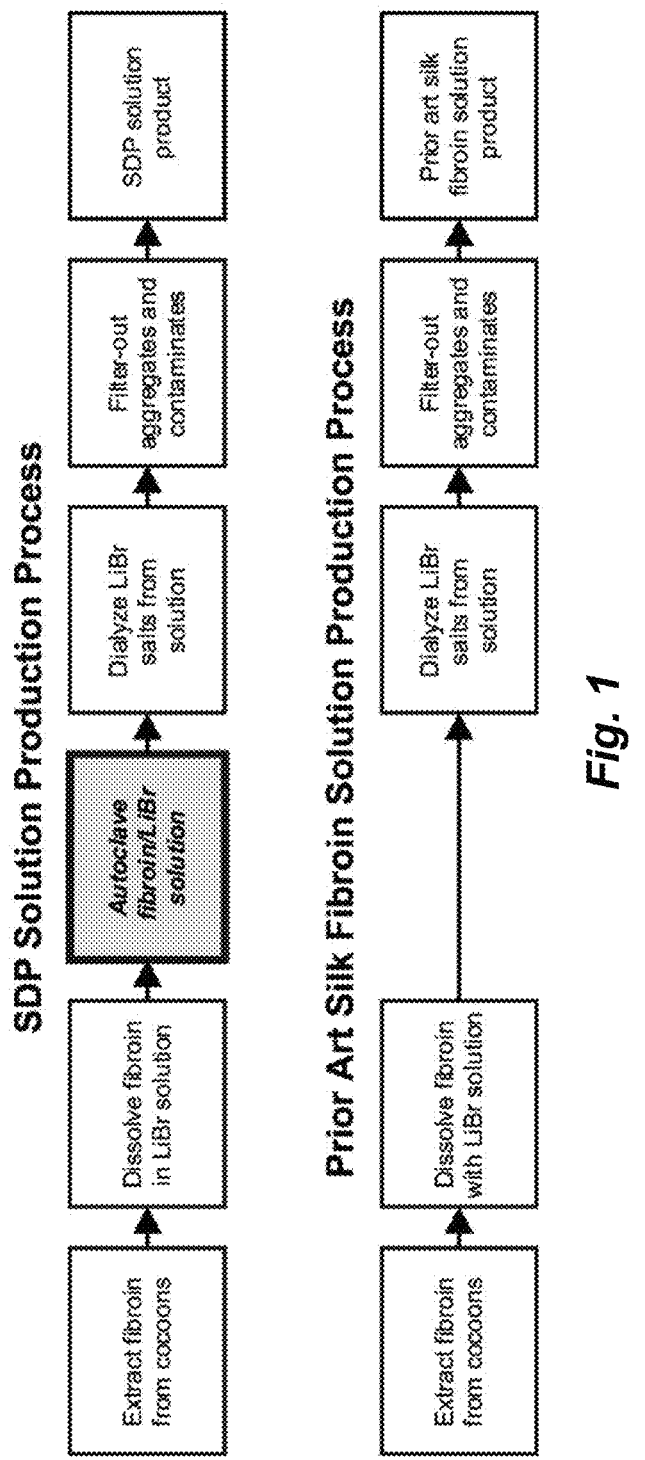
FIG. 1. Flowchart illustrating key processing steps for the generation of both SDP solution and prior art silk fibroin solution. The SDP Production Process contains an additional step (italicized in center) to enhance solution stability over time, which is not performed during the prior art silk fibroin solution production process.

The invention provides a protein composition derived from silk fibroin. The protein composition possesses enhanced solubility and stability in aqueous solutions. The primary amino acid sequence of native fibroin is modified in the fibroin-derived protein composition such that cysteine disulfide bonds between the fibroin heavy and fibroin light protein chains are reduced or eliminated. Additionally, the composition can have a serine content that is reduced by greater than 40% compared to native fibroin protein, and the average molecular weight of the proteins in the composition is less than about 100 kDa.

Definitions

The following definitions are included to provide a clear and consistent understanding of the specification and claims. As used herein, the recited terms have the following meanings. All other terms and phrases used in this specification have their ordinary meanings as one of skill in the art would understand. Such ordinary meanings may be obtained by reference to technical dictionaries, such as *Hawley's Condensed Chemical Dictionary* 14$^{th}$ Edition, by R. J. Lewis, John Wiley & Sons, New York, N.Y., 2001.

References in the specification to "one embodiment", "an embodiment", etc., indicate that the embodiment described may include a particular aspect, feature, structure, moiety, or characteristic, but not every embodiment necessarily includes that aspect, feature, structure, moiety, or characteristic. Moreover, such phrases may, but do not necessarily, refer to the same embodiment referred to in other portions of the specification. Further, when a particular aspect, feature, structure, moiety, or characteristic is described in connection with an embodiment, it is within the knowledge of one skilled in the art to affect or connect such aspect, feature, structure, moiety, or characteristic with other embodiments, whether or not explicitly described.

The singular forms "a," "an," and "the" include plural reference unless the context clearly dictates otherwise. Thus, for example, a reference to "a component" includes a plurality of such components, so that a component X includes a plurality of components X. It is further noted that the claims may be drafted to exclude an optional element. As such, this statement is intended to serve as antecedent basis for the use of exclusive terminology, such as "solely," "only," "other than", and the like, in connection with any element described herein, and/or the recitation of claim elements or use of "negative" limitations.

The term "and/or" means any one of the items, any combination of the items, or all of the items with which this term is associated. The phrases "one or more" and "at least one" are readily understood by one of skill in the art, particularly when read in context of its usage. For example, the phrase can mean one, two, three, four, five, six, ten, 100, or any upper limit approximately 10, 100, or 1000 times higher than a recited lower limit.

The term "about" can refer to a variation of ±5%, ±10%, ±20%, or ±25% of the value specified. For example, "about 50" percent can in some embodiments carry a variation from 45 to 55 percent. For integer ranges, the term "about" can include one or two integers greater than and/or less than a recited integer at each end of the range. Unless indicated otherwise herein, the term "about" is intended to include values, e.g., weight percentages, proximate to the recited range that are equivalent in terms of the functionality of the individual ingredient, element, the composition, or the embodiment. The term about can also modify the endpoints of a recited range as discuss above in this paragraph.

As will be understood by the skilled artisan, all numbers, including those expressing quantities of ingredients, properties such as molecular weight, reaction conditions, and so forth, are approximations and are understood as being optionally modified in all instances by the term "about." These values can vary depending upon the desired properties sought to be obtained by those skilled in the art utilizing the teachings of the descriptions herein. It is also understood that such values inherently contain variability necessarily resulting from the standard deviations found in their respective testing measurements.

As will be understood by one skilled in the art, for any and all purposes, particularly in terms of providing a written description, all ranges recited herein also encompass any and all possible sub-ranges and combinations of sub-ranges thereof, as well as the individual values making up the range, particularly integer values. A recited range (e.g., weight percentages or carbon groups) includes each specific value, integer, decimal, or identity within the range. Any listed range can be easily recognized as sufficiently describing and enabling the same range being broken down into at least equal halves, thirds, quarters, fifths, or tenths. As a non-limiting example, each range discussed herein can be readily broken down into a lower third, middle third and upper third, etc. As will also be understood by one skilled in the art, all language such as "up to", "at least", "greater than", "less than", "more than", "or more", and the like, include the number recited and such terms refer to ranges that can be subsequently broken down into sub-ranges as discussed above. In the same manner, all ratios recited herein also include all sub-ratios falling within the broader ratio. Accordingly, specific values recited for radicals, substituents, and ranges, are for illustration only; they do not exclude other defined values or other values within defined ranges for radicals and substituents.

One skilled in the art will also readily recognize that where members are grouped together in a common manner, such as in a Markush group, the invention encompasses not only the entire group listed as a whole, but each member of the group individually and all possible subgroups of the main group. Additionally, for all purposes, the invention encompasses not only the main group, but also the main group absent one or more of the group members. The invention therefore envisages the explicit exclusion of any one or more of members of a recited group. Accordingly, provisos may apply to any of the disclosed categories or embodiments whereby any one or more of the recited elements, species, or embodiments, may be excluded from such categories or embodiments, for example, for use in an explicit negative limitation.

The term "contacting" refers to the act of touching, making contact, or of bringing to immediate or close proximity, including at the cellular or molecular level, for example, to bring about a physiological reaction, a chemical reaction, or a physical change, e.g., in a solution, in a reaction mixture, in vitro, or in vivo.

For a therapeutic application, an "effective amount" refers to an amount effective to treat a disease, disorder, and/or condition, or to bring about a recited effect. For example, an effective amount can be an amount effective to reduce the progression or severity of the condition or symptoms being treated. Determination of a therapeutically effective amount is within the capacity of persons skilled in the art. The term "effective amount" is intended to include an amount of a composition described herein, or an amount of a combination of peptides described herein, e.g., that is effective to treat or prevent a disease or disorder, or to treat the symptoms of the disease or disorder, in a host. Thus, an "effective amount" generally means an amount that provides the desired effect.

For process and preparation applications, an "effective amount" refers to an amount effective to bring about a recited effect, such as an amount necessary to form products in a reaction mixture. Determination of an effective amount is typically within the capacity of persons skilled in the art, especially in light of the detailed disclosure provided herein. The term "effective amount" is intended to include an amount of a compound or reagent described herein, or an amount of a combination of compounds or reagents described herein, or conditions related to a process described herein, e.g., that is effective to form the desired products in a reaction mixture. Thus, an "effective amount" generally means an amount that provides the recited desired effect.

Fibroin is derived from the *Bombyx mori* silkworm cocoon. The protein fibroin includes a heavy chain that is about 350-400 kDa in molecular weight and a light chain that is about 25 kDa in molecular weight, wherein the heavy and light chains are linked together by a disulfide bond. The primary sequences of the heavy and light chains are known in the art. The fibroin protein chains possess hydrophilic N and C terminal domains, and alternating blocks of hydrophobic/hydrophilic amino acid sequences allowing for a mixture of steric and electrostatic interactions with surrounding molecules in solution. At low concentration dilutions (1% or less) the fibroin protein molecule is known to take on an extended protein chain form and not immediately aggregate in solution. The fibroin protein is highly miscible with hydrating molecules such as HA, PEG, glycerin, and CMC, has been found to be highly biocompatible, and integrates or degrades naturally within the body through enzymatic action. Native fibroin, or prior art silk fibroin (PASF), is known in the art and has been described by, for example, Daithankar et al. (*Indian J. Biotechnol.* 2005, 4, 115-121).

The terms "silk-derived protein" (SDP) and "fibroin-derived protein" are used interchangeably herein. These materials are prepared by the processes described herein involving heat, pressure, and a high concentration of a heavy salt solution. Therefore 'silk-derived' and 'fibroin-derived' refers to the starting material of the process that modifies the silk fibroin protein to arrive at a protein composition with the structural, chemical and physical properties described herein.

Fibroin-Derived Protein Composition Preparation.

The fibroin-derived protein composition described herein possesses enhanced stability compared to native fibroin in aqueous solutions. The enhanced stability achieved by the fibroin-derived protein composition, also referred herein as a silk-derived protein (SDP), allows the material to remain in solution significantly longer than the native/prior art silk fibroin proteins (referred to herein as PASF). The enhanced stability of the SDP material also allows for the preparation of SDP solutions of high concentration without aggregation, precipitation, or gelation. In commercial applications such as with food, beverage, eye drops, or applications requiring protein to be soluble in solution, the enhanced stability provides suitably lengthy shelf-life and increased quality of the product by reducing protein aggregation. Potential aggregation of protein in solution negatively impacts a product's desired performance for a particular application. The ability to concentrate the SDP to high constitutions in solution (over 50% w/v or >500 mg/mL) is significantly advantageous for inventorying a useful working solution that can be used as-is or diluted for any number of applications. Examples of such applications are the use of SDP as an ingredient in food, beverage, or ophthalmic formulations as a protein supplement or additive.

The enhanced stability in aqueous solutions is derived from transforming the primary amino acid sequences of the native fibroin protein into the SDP material. The changes in the primary sequence decrease the susceptibility of the molecules to aggregate. Aggregation eventually leads to gel formation. In the transformation of the native fibroin, both serine and cysteine amino acids are cleaved in the presence of high heat and dehydrating conditions. Similarly, Patchornik et al. (*J. Am. Chem. Soc.* 1964, 86, 1206) demonstrated that a dehydroalanine (DHA) intermediate is formed from serine and cysteine in solution. The amino acid degradation is further driven when in the presence of a strong dehydrating solvent system, such as the 50-55% w/v LiBr solution as described herein, in which a hydride shift takes place to induce removal of water. The degradation reaction can take place in the presence of hydroxide ions (e.g., pH 7.5 to pH 11), which further drives cleavage of the DHA intermediate. This cleavage forms an amide, a pyruvoyl peptide, and LiBr. One viable chemical mechanism is outlined in Scheme 1 for a serine amino acid, which scheme is also applicable for cysteine amino acids. Chemical alteration of the serine and cysteine amino acids of the PASF protein into a DHA intermediate with further hydrolytic cleavage leads to enhanced solution stability of the SDP products.

through disulfide linkages. These disulfide bridges participate in fibroin protein aggregation and gel network flocculation. Without the native fibroin light chain present, the proteins are significantly less susceptible to aggregation. Therefore, the process described herein effectively reduces the native fibroin light chain's ability to form disulfide bonds by reducing cysteine content and thus reducing or eliminating disulfide bond-forming capability. Through this mechanism, the transformative process described herein functionally stabilizes the resulting SDP in solution by reducing or eliminating the ability to form cysteine-derived aggregations.

In addition to aggregation-inducing disulfide bridges, the susceptibility of the silk fibroin to further aggregate into flocculated structure is also driven by the protein's amino acid chemistry as described by Mayen et al. (*Biophysical Chemistry* 2015, 197:10-17). Molecular modeling of silk fibroin serine, alanine, and glycine amino acid sequences have shown that the presence of serine enhances initial protein-to-protein interaction through a greater propensity to create hydrogen bonding between adjacent fibroin protein chain moieties. The models demonstrate that reduced serine and increased alanine and glycine decrease the initial propensity for protein aggregation. The molecular modeling observations indicate that by altering the native amino acid Scheme 1. Schematic detailing an underlying chemical reaction for serine and cysteine degradation. Degradation is driven by the production of a DHA intermediate that is formed from a hydride shift reaction in the presence of a dehydrating high salt concentration environment. Degradation of DHA then occurs through an $SN_2$ reaction within the basic solvent environment.

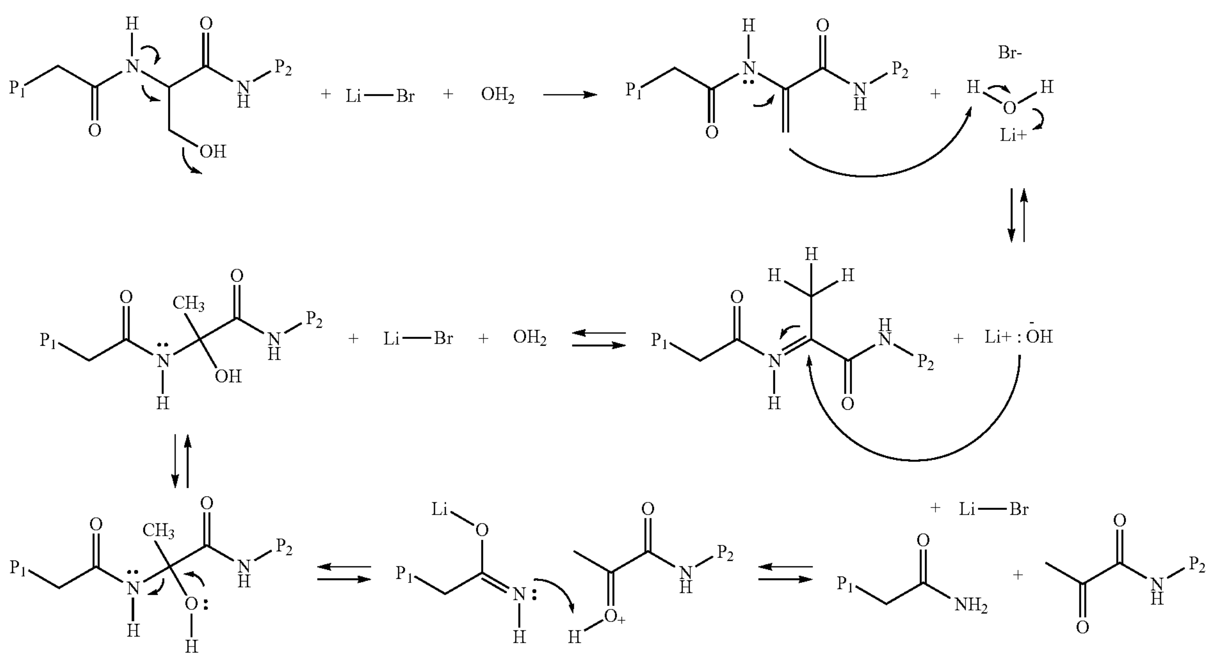

The cleavage reaction discussed above significantly affects macromolecular properties of the resulting peptides, which results in an aqueous solution of stabilized SDP material. The initial protein aggregation of fibroin is believed to be instigated by interactions of the native fibroin heavy and light chains at the cysteine amino acids as described by Greving et al. (*Biomacromolecules* 2012, 13(3): 676-682). The cysteine amino acids within the fibroin light and heavy protein chains interact with one another chemistry of the fibroin protein a material could be generated that would have higher stability in aqueous solution.

One strategy to accomplish enhanced stability is to eliminate charged functional groups, such as hydroxyls, from the protein. Due to the relatively high electronegativity of hydroxyl groups, this chemistry can drive both hydrogen bonding with available hydrogen atoms and non-specific charge interactions with positively charged amino acid groups. Almost 12% of the native fibroin protein's content is composed of serine, which bears a hydroxyl functional group. Therefore, by reducing the availability of hydroxyl groups that facilitate hydrogen bonding, the overall protein stability in solution may be enhanced. The process described herein effectively reduces the amount of serine content and increases the relative alanine and glycine content, which eliminates the number of available hydroxyl groups available to create hydrogen bonds. Through this mechanism the process described herein functionally stabilizes the resulting SDP in solution for extended periods of time (e.g., at least several [6-8] months, and/or for more than 1.5 years; extended studies are ongoing, indicating that stability may be maintained for more than 2 years, or more than 3 years).

In addition to the reduction of cysteine and serine moieties, solvent charge interaction is important for stabilizing a protein solution. After initial protein flocculation, the gelation process is believed to continue to drive closer associations among the native fibroin heavy chains, which leads to both intra- and inter-molecular beta-sheet formation among hydrophobic blocks of the heavy chains. Once significant beta-sheet formation occurs, the fibroin solution transitions to a gel. As the solution transitions to a gel, and the fibroin becomes insoluble and is no longer useful as a solution-based product. To prevent gelation, the pH of the SDP solution can be raised to high alkalinity to enhance stability, for example over a pH of 7.5. As a result, the increased pH produces additional free hydroxyl groups that form a valence shield around the SDP molecules in solution. The formed valence shield acts to produce a zeta potential that stabilizes the protein by reducing protein-protein interactions derived from hydrogen bonding or non-specific charged and/or hydrophobic interactions. The fibroin-transformation process functionally stabilizes processed SDP in solution through this mechanism and others.

SDP material can be prepared by the following process.

1. Silk cocoons are prepared by removing pupae material and pre-rinsing in warm water.
2. Native fibroin protein fibers are extracted from the gum-like sericin proteins by washing the cocoons in water at high water temperature, typically 95° C. or more, at an alkaline pH.
3. The extracted fibroin fibers are dried and then dissolved using a solvent system that neutralizes hydrogen bonding between the beta-sheets; a 54% LiBr aqueous solution of 20% w/v silk fibroin protein is effective for this neutralization step.
4. The dissolved fibroin protein in LiBr solution is processed in an autoclave environment (~121° C.[~250° F.], at ~15-17 PSI pressure, for approximately 30 minutes at temperature).
5. The heat processed fibroin protein and LiBr solution are then dialyzed to remove lithium and bromide ions from solution. At this point in the process the material has been chemically transformed to SDP.
6. The dialyzed SDP is then filtered to remove any non-dissolved aggregates and contaminating bioburden.

The SDP solution is produced using a distinctly different process than the process used for current silk fibroin solution production, as schematically illustrated in FIG. 1. Notably, the autoclaving of the silk fibroin protein while it is combined with LiBr in solution initiates chemical transitions to produce the stabilized SDP material. The fibroin protein is dissolved in LiBr solution, which neutralizes hydrogen bonding and electrostatic interactions of the solubilized native fibroin protein. This leaves the protein without specific secondary structure confirmations in solution. As a result, the thermodynamic energy required to hydrolyze covalent bonding within the fibroin protein chain is at its lowest energy requirements to initiate hydrolytic cleavage.

In one embodiment the temperature is set to 121° C. for 30 minutes at 15-17 PSI autoclave conditions. However, in various embodiments, the processing conditions may be modified to stabilize the SDP material to varying degrees. In other embodiments, additional protein solubilization agents can be used in the process, including other or additional halide salts such as calcium chloride and sodium thiocyanate, organic agents such as urea, guanidine hydrochloride, and 1,1,1,3,3,3-hexafluoroisopropanol, additional strong ionic liquid solution additives such as calcium nitrate and 1-butyl-3-methylimidazolium chloride, or a combination thereof.

Fibroin-Derived Protein Compositions.

The invention provides a protein composition derived from silk fibroin, which composition possesses enhanced solubility and stability in aqueous solutions. In one embodiment, the invention provides a protein composition prepared by a process comprising heating an aqueous fibroin solution at an elevated pressure. The aqueous fibroin solution includes lithium bromide at a concentration of at least 8M. The aqueous fibroin solution is heated to at least about 105° C. (221° F.) under a pressure of at least about 10 PSI for at least about 20 minutes, to provide the protein composition. The polypeptides of the protein composition comprise less than 8.5% serine amino acid residues, and the protein composition has an aqueous viscosity of less than 5 cP as a 10% w/w solution in water.

In other embodiments, the invention provides a protein composition prepared by a process comprising heating an aqueous fibroin solution at an elevated pressure, wherein the aqueous fibroin solution comprises lithium bromide at a concentration of 9-10M, and wherein the aqueous fibroin solution is heated to a temperature in the range of about 115° C. (239° F.) to about 125° C. (257° F.), under a pressure of about 15 PSI to about 20 PSI for at least about 20 minutes; to provide the protein composition. The protein composition can include less than 6.5% serine amino acid residues and the protein composition can have an aqueous viscosity of less than 10 cP as a 15% w/w solution in water.

The invention also provides a fibroin-derived protein composition that possesses enhanced stability in aqueous solution, wherein: the primary amino acid sequences of the fibroin-derived protein composition differs from native fibroin by at least by at least 4% with respect to the combined difference in serine, glycine, and alanine content (fibroin-derived vs. PASF); cysteine disulfide bonds between the fibroin heavy and fibroin light protein chains are reduced or eliminated; and the composition has a serine content that is reduced by greater than 25% compared to native fibroin protein. The average molecular weight of the fibroin-derived protein composition can be less than about 100 kDa and greater than about 15 kDa.

In another embodiment, the invention provides a fibroin-derived protein composition that possesses enhanced stability in aqueous solution, wherein: the primary amino acid sequences of the fibroin-derived protein composition differs from native fibroin by at least by at least 6% with respect to the combined difference in serine, glycine, and alanine content; cysteine disulfide bonds between the fibroin heavy and fibroin light protein chains are reduced or eliminated; and the composition has a serine content that is reduced by greater than 40% compared to native fibroin protein. The average molecular weight of the fibroin-derived protein composition can be less than about 96 kDa and greater than about 15 kDa.

The invention further provides a fibroin-derived protein composition that possesses enhanced stability in aqueous solutions, wherein: the primary amino acid sequences of the fibroin-derived protein composition is modified from native silk fibroin; cysteine disulfide bonds between the fibroin heavy and fibroin light protein chains are reduced or eliminated; the average molecular weight of the fibroin-derived protein composition is less than about 100 kDa and greater than about 15 kDa; and the fibroin-derived protein composition maintains an optical absorbance at 550 nm of less than 0.25 for at least two hours after five seconds of ultrasonication. For example, a 5% w/w solution of the protein composition can maintain an optical absorbance of less than 0.1 at 550 nm after five seconds of ultrasonication at 10 Hz and 20% amplitude, which are the standard conditions used for ultrasonication described herein.

In another embodiment, the invention provides a fibroin-derived protein composition that possesses enhanced stability in aqueous solutions, wherein: the primary amino acid sequences of the fibroin-derived protein composition is modified from native silk fibroin such that they differ from native fibroin by at least by at least 5% with respect to the combined difference in serine, glycine, and alanine content; cysteine disulfide bonds between the fibroin heavy and fibroin light protein chains are reduced or eliminated; the average molecular weight of the fibroin-derived protein composition is less than about 96 kDa and greater than about 15 kDa; and the fibroin-derived protein composition maintains an optical absorbance at 550 nm of less than 0.2 for at least two hours after five seconds of ultrasonication.

In various embodiments, the fibroin-derived protein composition can be isolated and/or purified as a dry powder or film, for example, by dialysis and/or filtration. Alternatively, the fibroin-derived protein composition can be isolated and/or purified as a stable aqueous solution, which can be modified for use as a food or beverage composition, or as a therapeutic formulation, such as an ophthalmic formulation. The invention therefore also provides a food or beverage composition that includes a protein composition described herein and a food or beverage component. Food components can include one or more of simple sugars, disaccharides, carbohydrates, fats, oils, vitamins, minerals, and water. Beverage components can include one or more of water, a coloring agent (e.g., a synthetic colorant, or a natural colorant such as saffron), vitamins, and minerals.

In various embodiments, the amino acid composition of the fibroin-derived protein differs from the amino acid composition of native fibroin by at least by at least 4%, by at least 4.5%, by at least 5%, or by at least 5.5%, or by at least 6%, with respect to the content of serine, glycine, and alanine combined.

The composition can have a serine content that is reduced by greater than 25%, by greater than 30%, by greater than 35%, by greater than 40%, or by greater than 45%, compared to the serine content of native fibroin protein.

The average molecular weight of the fibroin-derived protein composition can be less than about 100 kDa, less than about 98 kDa, less than about 96 kDa, less than about 95 kDa, less than about 90 kDa, less than about 85 kDa, less than about 80 kDa, less than about 75 kDa, or less than about 70 kDa. In various embodiments, the average molecular weight of the fibroin-derived protein composition can be greater than about 30 kDa, greater than about 35 kDa, greater than about 40 kDa, greater than about 50 kDa, greater than about 60 kDa, or greater than about 70 kDa. Accordingly, the (weight average) average molecular weight of the fibroin-derived protein composition can be about 30 kDa to about 100 kDa, about 30 kDa to about 96 kDa, 30 kDa to about 90 kDa, about 35 kDa to about 80 kDa, about 35 kDa to about 70 kDa, about 40 kDa to about 60 kDa. In various embodiments, the average molecular weight of the fibroin-derived protein composition is about 60 kDa to about 80 kDa, about 50 kDa to about 70 kDa, about 40 kDa to about 60 kDa, about 30 kDa to about 50 kDa, about 35 kDa to about 45 kDa, or about 40 kDa to about 43 kDa.

In various embodiments, the protein composition has an aqueous viscosity of less than 4 cP as a 10% w/w solution in water. In additional embodiments, the protein composition has an aqueous viscosity of less than 10 cP as a 24% w/w solution in water.

In some embodiments, the protein composition is soluble in water at 40% w/w without any precipitation observable by ocular inspection.

In various embodiments, the protein composition does not gel upon ultrasonication of an aqueous solution of the protein composition at concentrations of up to 10% w/w. In additional embodiments, the protein composition does not gel upon ultrasonication of an aqueous solution of the protein composition at concentrations of up to 15% w/w, up to 20% w/w, up to 25% w/w, up to 30% w/w, up to 35% w/w, or up to 40% w/w.

In some embodiments, the protein composition comprises less than 8% serine amino acid residues. In other embodiments, the protein composition comprises less than 7.5% serine amino acid residues, less than 7% serine amino acid residues, less than 6.5% serine amino acid residues, or less than 6% serine amino acid residues.

In some embodiments, the protein composition comprises greater than 46.5% glycine amino acids, relative to the total amino acid content of the protein composition. In other embodiments, the protein composition comprises greater than 47% glycine amino acids, greater than 47.5% glycine amino acids, or greater than 48% glycine amino acids.

In some embodiments, the protein composition comprises greater than 30% alanine amino acids, relative to the total amino acid content of the protein composition. In other embodiments, the protein composition comprises greater than 30.5% alanine, greater than 31% alanine, or greater than 31.5% alanine.

In some embodiments, the protein composition completely re-dissolves after being dried to a thin film. In various embodiments, the protein composition lacks beta-sheet protein structure in aqueous solution. In certain embodiments, the protein composition maintains an optical absorbance in aqueous solution of less than 0.25 at 550 nm after at least five seconds of ultrasonication.

In some embodiments, protein composition is in combination with water. The protein composition can completely dissolve in water at a concentration of 10% w/w, or even greater concentrations such as 15% w/w, 20% w/w, 25% w/w, 30% w/w, 35% w/w, or 40% w/w. In some embodiments, the protein composition can be isolated and purified, for example, by dialysis, filtration, or a combination thereof.

In various embodiments, the protein composition enhances the spreading of an aqueous solution comprising the protein composition and ophthalmic formulation components, for example, compared to the spreading of a corresponding composition that does not include the protein composition. The enhanced spreading can result in an increase in surface area of the aqueous solution by greater than twofold, or greater than threefold.

In some embodiments, the protein composition does not form a gel at concentrations up to 20% w/v, up to 30% w/v, or up to 40% w/v. The protein composition can remain in solution up to a viscosity of at least 9.8 cP.

In some embodiments, the fibroin-derived protein composition can have glycine-alanine-glycine-alanine (GAGA) (SEQ ID NO: 1) segments of amino acids that comprise at least about 47.5% of the amino acids of the fibroin-derived protein composition. The fibroin-derived protein composition can also have glycine-alanine-glycine-alanine (GAGA) (SEQ ID NO: 1) segments of amino acids that comprise at least about 48%, at least about 48.5%, at least about 49%, at least about 49.5%, or at least about 50%, of the amino acids of the protein composition.

In various embodiments, the fibroin-derived protein composition can have glycine-alanine (GA) segments of amino acids that comprise at least about 59% of the amino acids of the fibroin-derived protein composition. The fibroin-derived protein composition can also have glycine-alanine (GA) segments of amino acids that comprise at least about 59.5%, at least about 60%, at least about 60.5%, at least about 61%, or at least about 61.5%, of the amino acids of the protein composition.

In another embodiment, the primary amino acid sequences of the fibroin-derived protein composition differs from native fibroin by at least by at least 6% with respect to the combined difference in serine, glycine, and alanine content; the average molecular weight of the fibroin-derived protein composition is less than about 100 kDa; and the fibroin-derived protein composition maintains an optical absorbance at 550 nm of less than 0.25 for at least two hours after five seconds of ultrasonication. Thus, in one specific embodiment, the invention provides a fibroin-derived protein composition that possesses enhanced stability in aqueous solution, wherein: the primary amino acid sequences of the fibroin-derived protein composition differs from native fibroin by at least by at least 6% with respect to the combined difference in serine, glycine, and alanine content; cysteine disulfide bonds between the fibroin heavy and fibroin light protein chains are reduced or eliminated; the composition has a serine content that is reduced by greater than 40% compared to native fibroin protein; and wherein the average molecular weight of the fibroin-derived protein composition is less than about 96 kDa.

In another embodiment, the invention provides a fibroin-derived protein composition that possesses enhanced stability in aqueous solutions, wherein: the primary amino acid sequences of the fibroin-derived protein composition is modified from native silk fibroin; cysteine disulfide bonds between the fibroin heavy and fibroin light protein chains are reduced or eliminated; the average molecular weight of the fibroin-derived protein composition is less than about 100 kDa; and the fibroin-derived protein composition maintains an optical absorbance at 550 nm of less than 0.25 for at least two hours after five seconds of ultrasonication. In one specific embodiment, the primary amino acid sequences of the fibroin-derived protein composition is modified from native silk fibroin such that they differ from native fibroin by at least by at least 5% with respect to the combined difference in serine, glycine, and alanine content; the average molecular weight of the fibroin-derived protein composition is less than about 96 kDa; and the fibroin-derived protein composition maintains an optical absorbance at 550 nm of less than 0.2 for at least two hours after five seconds of ultrasonication.

Thus, in one specific embodiment, the invention provides a fibroin-derived protein composition that possesses enhanced stability in aqueous solutions, wherein: the primary amino acid sequences of the fibroin-derived protein composition is modified from native silk fibroin such that they differ from native fibroin by at least by at least 5% with respect to the combined difference in serine, glycine, and alanine content; cysteine disulfide bonds between the fibroin heavy and fibroin light protein chains are reduced or eliminated; the average molecular weight of the fibroin-derived protein composition is less than about 96 kDa; and the fibroin-derived protein composition maintains an optical absorbance at 550 nm of less than 0.2 for at least two hours after five seconds of ultrasonication.

The invention also provides a protein composition prepared by a process comprising heating an aqueous fibroin solution at an elevated pressure, wherein the aqueous fibroin solution comprises lithium bromide at a concentration of at least 8M, and wherein the aqueous fibroin solution is heated to at least about 105° C. (221° F.) under a pressure of at least about 10 PSI for at least about 20 minutes; to provide the protein composition, wherein the protein composition comprises less than 8.5% serine amino acid residues and the protein composition has an aqueous viscosity of less than 5 cP as a 10% w/w solution in water. Therefore, the invention provides a method of preparing a fibroin-derived protein composition comprising one or more of the process steps described herein.

In one embodiment, the concentration of lithium bromide is about 8.5M to about 11M. In some embodiments, the concentration of lithium bromide is about 9M to about 10M, or about 9.5 M to about 10 M.

In some embodiments, the aqueous fibroin solution that contains lithium bromide is heated to at least about 107° C. (225° F.), at least about 110° C. (230° F.), at least about 113° C. (235° F.), at least about 115° C. (239° F.), or at least about 120° C. (248° F.).

In some embodiments, the aqueous fibroin solution that contains lithium bromide is heated under a pressure of at least about 12 PSI, at least about 14 PSI, at least about 15 PSI, or at least about 16 PSI, up to about 18 PSI, or up to about 20 PSI.

In some embodiments, the aqueous fibroin solution that contains lithium bromide is heated for at least about 20 minutes, at least about 30 minutes, at least about 45 minutes, or at least about 1 hour, up to several (e.g., 12-24) hours.

In some embodiments, the protein composition has an aqueous viscosity of less than 4 cP as a 10% w/w solution in water. In various embodiments, the protein composition has an aqueous viscosity of less than 10 cP as a 24% w/w solution in water.

In some embodiments, the protein composition can be dissolved in water at 40% w/w without observable precipitation.

In some embodiments, the fibroin has been separated from sericin.

In some embodiments, lithium bromide has been removed from the protein composition to provide a purified protein composition. In various embodiments, the protein composition has been isolated and purified, for example, by dialysis, filtration, or a combination thereof.

In various embodiments, the protein composition does not gel upon ultrasonication of an aqueous solution of the composition at concentrations of up to 10% w/w, up to 15% w/w, up to 20% w/w, up to 25% w/w, up to 30% w/w, up to 35% w/w, or up to 40% w/w.

In additional embodiments, the protein composition has properties as described above, and amino acid compositions as described above regarding serine, glycine, and alanine content.

In various embodiments, the protein composition re-dissolves after drying as a thin film. The protein composition can lack beta-sheet protein structure in solution. The protein composition can maintain an optical absorbance in solution of less than 0.25 at 550 nm after at least five seconds of ultrasonication.

In one specific embodiment, the invention provides a protein composition prepared by a process comprising heating an aqueous fibroin solution at an elevated pressure, wherein the aqueous fibroin solution comprises lithium bromide at a concentration of 9-10 M, and wherein the aqueous fibroin solution is heated to a temperature in the range of about 115° C. (239° F.) to about 125° C. (257° F.), under a pressure of about 15 PSI to about 20 PSI for at least about 30 minutes; to provide the protein composition, wherein the protein composition comprises less than 6.5% serine amino acid residues and the protein composition has an aqueous viscosity of less than 10 cP as a 15% w/w solution in water.

Further embodiments of the invention are described herein below.

The invention provides a novel silk-derived protein (SDP) composition that is chemically distinct from native silk fibroin protein. The SDP has enhanced stability in aqueous solution. The SDP can be used in a method for forming a food composition, a beverage, or an ophthalmic formulation comprising combining food, beverage, or ophthalmic ingredients with a protein composition described herein, for example, a protein composition aqueous solution. The solution can include about 0.01% to about 92% w/v SDP. The solution can be about 8% to about 99.9% w/v water.

In one embodiment, the SDP material with enhanced solution stability can be used as an ingredient in a beverage for human or animal consumption, such as an ingredient or additive in a sports drink, nutrient drink, soft drink, or in bottled water. In another embodiment, the SDP material with enhanced solution stability can be used as an ingredient in a food product, such as in dairy products, cereal, or processed foods. In yet another embodiment, the SDP material with enhanced solution stability can be used as an ingredient in an eye drop formulation, such as in artificial tears, ocular lubricants, lid scrubs, or therapeutic formulations.

In one aspect, the invention provides a process that induces hydrolysis, amino acid degradation, or a combination thereof, of fibroin protein such that the average molecular weight of the protein is reduced from about 100-200 kDa for silk fibroin produced using prior art methods to about 30-90 kDa, or about 30-50 kDa, for the SDP material described herein. The resulting polypeptides can be a random assortment of peptides of various molecular weights averaging to the ranges recited herein. In addition, the amino acid chemistry can be altered by reducing cysteine content to non-detectable levels by standard assay procedures. For example, the serine content can be reduced by over 50% from the levels found in the native fibroin, which can result in increases of overall alanine and glycine content by 5% (relative amino acid content), as determined by standard assay procedures. The process can provide a protein composition where the fibroin light chain protein is not discernable after processing, as well when the sample is run using standard SDS-PAGE electrophoresis methods. Furthermore, the resulting SDP material forms minimal to no beta-sheet protein secondary structure post-processing, while silk fibroin solution produced using prior art methods forms significant amounts of beta-sheet secondary structure. In one embodiment, the SDP material can be prepared by processing silk fibroin fibers under autoclave or autoclave-like conditions (i.e., approximately 120° C. and 14-18 PSI) in the presence of a 40-60% w/v lithium bromide (LiBr) solution.

In some embodiments, the invention provides a food or beverage product that includes the SDP as an ingredient. The SDP can serve to provide additional protein content, resulting in improved nutritional value, health benefits, and/or therapeutic advantages to the human or animal that consumes the food or beverage. In one embodiment, the SDP is included in a beverage such as water, a sport drink, an energy drink, or a carbonated drink. In another embodiment, the SDP is included in food products such as yogurt, energy bars, cereal, bread, or pasta.

The food or beverage product can include an effective amount of SDP, such as about 0.01% by weight to about 92% by weight of SDP. In various embodiments, the SDP can be present in about 0.1% by weight to about 30% by weight, about 0.5% by weight to about 20% by weight, or about 1% by weight to about 10% by weight. In certain specific embodiments, the SDP can be derived from *Bombyx mori* silkworm fibroin.

In another embodiment, the invention provides an ophthalmic composition for the treatment of dry eye syndrome in a human or mammal. The composition can be an aqueous solution that includes an amount of SDP effective for treating dry eye syndrome. For example, the aqueous solution can include about 0.01% by weight to about 80% by weight SDP. In other embodiments, the aqueous solution can include SDP at about 0.1% by weight to about 10% by weight, or about 0.5% by weight to about 2% by weight. In certain specific embodiments, the ophthalmic composition can include about 0.05% w/v SDP, about 0.1% w/v SDP, about 0.2% w/v SDP, about 0.25% w/v SDP, about 0.5% w/v SDP, about 0.75% w/v SDP, about 1% w/v SDP, about 1.5% w/v SDP, about 2% w/v SDP, about 2.5% w/v SDP, about 5% w/v SDP, about 8% w/v SDP, or about 10% w/v SDP. The SDP can be derived from *Bombyx mori* silkworm fibroin.

In various embodiments, the ophthalmic formulation can include additional components in the aqueous solution, such as a demulcent agent, a buffering agent, and/or a stabilizing agent. The demulcent agent can be, for example, hyaluronic acid (HA), hydroxyethyl cellulose, hydroxypropyl methylcellulose, dextran, gelatin, a polyol, carboxymethyl cellulose (CMC), polyethylene glycol, propylene glycol (PG), hypromellose, glycerin, polysorbate 80, polyvinyl alcohol, or povidone. The demulcent agent can be present, for example, at about 0.01% by weight to about 10% by weight, or at about 0.2% by weight to about 2% by weight. In one specific embodiment, the demulcent agent is HA. In various embodiments, the HA can be present at about 0.2% by weight of the formulation.

The buffering or stabilizing agent of an ophthalmic formulation can be phosphate buffered saline, borate buffered saline, citrate buffer saline, sodium chloride, calcium chloride, magnesium chloride, potassium chloride, sodium bicarbonate, zinc chloride, hydrochloric acid, sodium hydroxide, edetate disodium, or a combination thereof.

An ophthalmic formulation can further include an effective amount of an antimicrobial preservative. The antimicrobial preservative can be, for example, sodium perborate, polyquaterium-1 (e.g., Polyquad® preservative), benzalkonium (BAK) chloride, sodium chlorite, brimonidine, brimonidine purite, polexitonium, or a combination thereof.

An ophthalmic formulation can also include an effective amount of a vasoconstrictor, an antihistamine, or a combination thereof. The vasoconstrictor or antihistamine can be naphazoline hydrochloride, ephedrine hydrochloride, phenylephrine hydrochloride, tetrahydrozoline hydrochloride, pheniramine maleate, or a combination thereof.

In one embodiment, an ophthalmic formulation can include an effective amount of fibroin-derived protein as described herein in combination with water and one or more ophthalmic components. The ophthalmic components can be, for example, a) polyvinyl alcohol; b) PEG-400 and hyaluronic acid; c) PEG-400 and propylene glycol, d) CMC and glycerin; e) propylene glycol and glycerin; f) glycerin, hypromellose, and PEG-400; or a combination of any one or more of the preceding components. The ophthalmic formulation can include one or more inactive ingredients such as HP-guar, borate, calcium chloride, magnesium chloride, potassium chloride, zinc chloride, and the like. The ophthalmic formulation can also include one or more ophthalmic preservatives such as sodium chlorite (Purite® preservative ($NaClO_2$), polyquad, BAK, EDTA, sorbic acid, benzyl alcohol, and the like. Ophthalmic components, inactive ingredients, and preservatives can be included at about 0.1% to about 5% w/v, such as about 0.25%, 0.3%, 0.4%, 0.5%, 1%, 2%, 2.5%, or 5%, or a range in between any two of the aforementioned values.

Accordingly, the invention provides a silk derived protein (SDP) composition that possesses enhanced stability in aqueous solutions in which the primary amino acid sequence of native fibroin is modified from native silk fibroin, wherein cysteine disulfide bonds between the fibroin heavy and fibroin light protein chains reduced or eliminated; wherein the composition has a serine content that is reduced by greater than 40% compared to native fibroin protein; and wherein the average molecular weight of the silk derived protein is less than about 96 kDa.

The invention also provides an ophthalmic formulation for the treatment of ophthalmic disorders in a human or mammal, wherein the ophthalmic formulation comprises water and an effective amount of the SDP as described above. The invention further provides an ophthalmic composition for use as an eye treatment in a human or mammal, wherein the ophthalmic composition comprises water, one or more of a buffering agent and stabilizing agent, and an effective amount of the SDP as described above.

The SDP is highly stable in water, where shelf-life solution stability is more than twice that of native silk fibroin in solution. For example, the SDP is highly stable in water, where shelf-life solution stability is more than 10 times greater compared to native silk fibroin in solution. The SDP material, when in an aqueous solution, does not gel upon sonication of the solution at a 5% (50 mg/mL) concentration. In other embodiments, the SDP material, when in an aqueous solution, does not gel upon sonication of the solution at a 10% (100 mg/mL) concentration.

The SDP material can have the fibroin light chain over 50% removed when compared to native silk fibroin protein. The SDP material can have a serine amino acid content of less than about 8% relative amino acid content, or a serine amino acid content of less than about 6% relative amino acid content.

The SDP material can have a glycine amino acid content above about 46.5%. The SDP material can have an alanine amino acid content above about 30% or above about 30.5%. The SDP material can have no detectable cysteine amino acid content, for example, as determined by HPLC analysis of the hydrolyzed polypeptide of the protein composition.

The SDP material can form 90% less, 95% less, or 98% less beta-sheet secondary protein structures as compared to native silk fibroin protein, for example, as determined by the FTIR analysis described in Example 8 below.

The invention additionally provides an ophthalmic composition for use as an eye treatment in a human or mammal, the composition comprising an aqueous solution including an effective amount of SDP material as described above, and a buffering or stabilizing agent.

The invention yet further provides an ophthalmic formulation for the treatment of ophthalmic disorders in human or mammal, the composition comprising an aqueous solution including an effective amount of SDP material with enhanced stability as described herein.

The invention also provides a method for forming a beverage mixture, a food composition, or an ophthalmic composition, with silk protein comprising combining a food, beverage, or ophthalmic components with the fibroin-derived protein composition described herein.

The following Examples are intended to illustrate the above invention and should not be construed as to narrow its scope. One skilled in the art will readily recognize that the Examples suggest many other ways in which the invention could be practiced. It should be understood that numerous variations and modifications may be made while remaining within the scope of the invention.

EXAMPLES

Example 1. Silk-Derived Protein Preparation and the Lawrence Stability Test

Materials. Silkworm cocoons were obtained from Tajima Shoji Co., Ltd., Japan. Lithium bromide (LiBr) was obtained from FMC Lithium, Inc., NC. An autoclave was obtained from Tuttnauer Ltd., NY. The 3,500 Da molecular-weight cutoff (MWCO) dialysis membranes were obtained from ThermoScientific, Inc., MA. An Oakton Bromide ($Br^-$) double-junction ion-selective electrode was obtained from ISE, Oakton Instruments, IL.

Processing. Two samples, SDP and prior art silk fibroin, were prepared as illustrated in FIG. 1. Briefly, SDP was produced by submerging pupae-free, cut silkworm cocoons (3-5 cuts/cocoon) into 95° C. heated, deionized water ($diH_2O$) containing 0.3 wt % $NaCO_3$ at 233 mL water/gram of cocoons. Cocoons were agitated in this solution for 75 minutes to dissolve sericin, thereby separating it from the silk fibers. The cocoons were subsequently washed four times in like dilutions of $diH_2O$ for 20 minutes per rinse to remove residual sericin from the washed silk fibers. The fibers were then dried in a convection oven at 60° C. for 2 hours, weighed, and dissolved in 54 wt % LiBr in water at a ratio of 4× LiBr volume per gram of extracted fiber. This solution was covered and then warmed in a convection oven at 60° C. for 2 hours to expedite extracted fiber dissolution. The solution was then placed in an autoclave and exposed to sterilization conditions (121° C., 17 PSI, 90-100% humidity) for 30 minutes to facilitate fibroin transformation. The resulting solution was allowed to cool to room temperature, then diluted to 5% fibroin with $diH_2O$ and dialyzed to remove LiBr salts using a 3,500 Da MWCO membrane. Multiple exchanges were performed in $diH_2O$ until Br ions were less than 1-ppm as determined in the hydrolyzed fibroin solution read on an Oakton Bromide ($Br^-$) double-junction ion-selective electrode. The solution was then further filtered using a 1-5 μm porosity filter followed by filtration through a 0.2 μm polishing filter. This product is referred to as 'SDP Solution' in FIG. 2.

Figure 2:
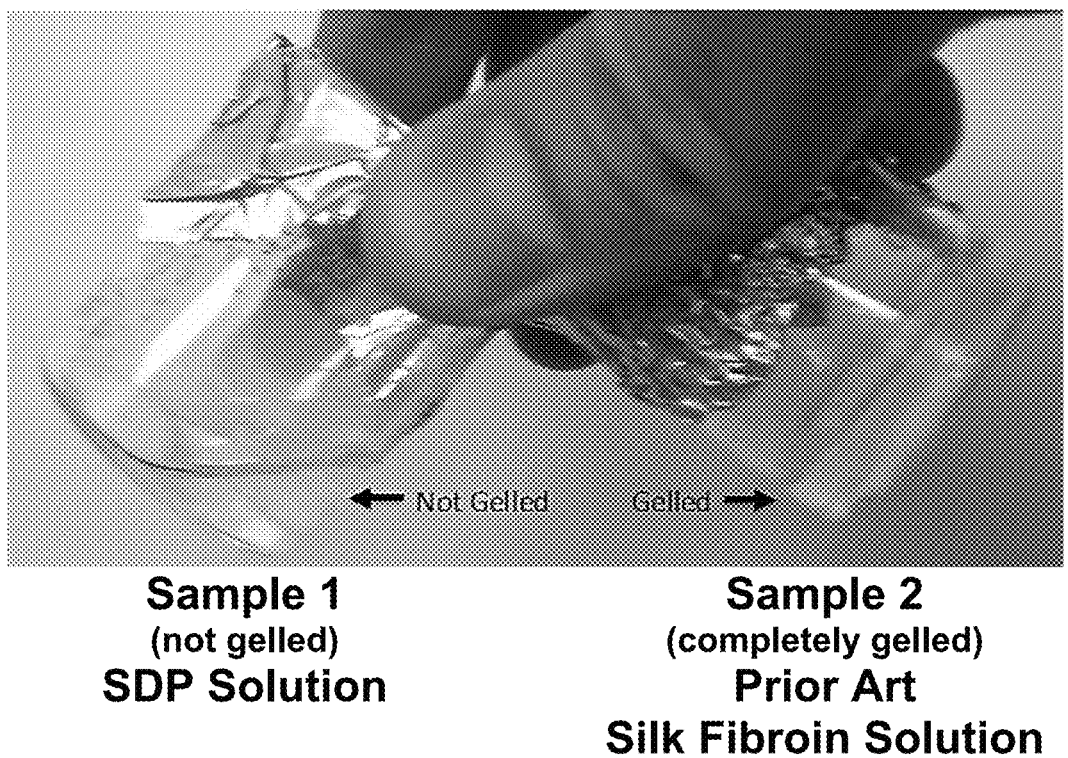
FIG. 2. Picture showing results of the Lawrence Stability Test for a stable SDP solution (Sample 1, on left, produced by the process described in Example 1), and a prior art silk fibroin solution (Sample 2, on right, produced by standard hydrolysis conditions). Visual inspection reveals that Sample 1 is a stable aqueous solution that has not gelled, while Sample 2 has gelled, and therefore is not a stable aqueous solution.

A 'control' silk fibroin solution was prepared as illustrated in FIG. 1 to provide the 'Prior Art Silk Fibroin Solution' shown in FIG. 2. Except for the autoclave step, the same process was performed as described above. A sampling volume (5 mL) from each sample was placed in separate 20 mL glass beakers and the beakers were sealed with foil. The samples were then subjected to the Lawrence Stability Test.

The Lawrence Stability Test is performed by placing the aqueous protein test solution (5% w/v, 50 mg/mL) within the autoclave chamber. The autoclave is then activated for a cycle at 121° C., 17 PSI, for 30 minutes, at 97-100% humidity. After completion of the cycle, the solution is allowed to cool and is then removed from the autoclave chamber. The solution is then shaken to observe solution gelation behavior. If the solution has gelled upon shaking for ~10 seconds, the sample fails the Lawrence Stability Test. Failing the test indicates that the material is inherently unstable as a protein solution.

The Lawrence Stability Test was performed on both the SDP Solution and the Prior Art Silk Fibroin Solution. The Prior Art Silk Fibroin Solution sample gelled immediately and therefore failed the Lawrence Stability Test. Conversely, the SDP Solution sample remained in solution indefinitely and therefore passed the Lawrence Stability Test. The lack of gelation can be attributed to the fact that SDP Solution production incorporated the autoclave-processing step as indicated in FIG. 1 above. An image of the different test results (not-gelled vs. gelled) is shown in FIG. 2.

Example 2. Silk-Derived Protein Molecular Weight Characterization

To evaluate the effect of processing on the molecular weight distribution of solubilized protein, SDP Solution and Prior Art Silk Fibroin Solution were subjected to polyacrylamide gel electrophoresis (PAGE), which separates proteins by molecular weight. Specifically, 15 μg of each sample was mixed with running buffer containing sodium dodecyl sulfate and dithiothreitol (Biorad Inc., CA) to remove any secondary folding structures and disulfide bonds, respectively. The mixtures were then heated to 70° C. for 5 minutes. The mixtures were loaded along with a 2.5-200 kDa molecular weight ladder (Life Technologies, CA) onto pre-cast, 4-12% polyacrylamide gradient gels containing Bis-Tris buffer salts (Life Technologies, CA), and then exposed to 120V electric field for 90 minutes on a BioRad PowerPac Power supply (BioRad Inc., CA). The gels were then removed and placed in Coomassie Blue stain for 12 hours to stain proteins, followed by 6 hours of washing in diH$_2$O. The gels were then scanned on a Biorad GS-800 Calibrated Desitometer (BioRad Inc., CA).

The resulting gel is shown in FIG. 3. The results show that the processing employed to prepare the SDP solution significantly shifts the average molecular weight from 150-200 kDa to less than 80 kDa (FIG. 3). The shift in molecular weight clearly indicates a transformation of the primary and/or secondary structure of the original native fibroin. In addition, the fibroin light chain of fibroin is not present in the SDP after the autoclaving process (visible at 23-26 kDa in Lane 2 for the prior art fibroin), which indicates that the fibroin light chain portion of the protein has been degraded or removed by the processing. These results demonstrate that the autoclave processing transforms the native fibroin protein to a new material that has smaller peptide fragments than the native fibroin protein. The process further degrades/ modifies the fibroin light chain. These transformations result in an SDP material that possesses enhanced solution stability as a result of these chemical changes.

Example 3. Silk-Derived Protein Stability Study

To further determine the functional impact of the autoclave process on the stability of the resulting SDP compared to the stability of prior art fibroin, the samples were analyzed using the methods of Wang et al. (*Biomaterials* 2008, 29(8): 1054-1064) to mimic a well-characterized model of silk fibroin protein gelation. Volumes of both samples (0.5 mL, SDP and PASF) were added to 1.7 mL clear centrifuge tubes and were subjected to ultrasonication (20% amplitude, 10 Hz, 15 seconds). The clear tubes containing the solutions were then visually monitored for gel formation as a screen for gelation.

The SDP Solution samples failed to form gels, as shown in FIG. 4A. Even 3 months post-sonication, the SDP samples remained in solution and lacked protein aggregation as determined by visual inspection. The Prior Art Silk Fibroin Solution sample gelled rapidly (within 2 hours) following sonication. The resulting gelled Prior Art Silk Fibroin is shown in FIG. 4B. These results further indicate that the autoclave process transforms the prior art fibroin to a new material and induces stability to the resulting SDP material.

Example 4. Impact of Heating on the Viscosity Profile of Aqueous Silk Solutions

The physicochemical properties of PASF and SDP were investigated, with particular attention paid to the impact of protein concentration on solution viscosity. It has been shown by Zafar et al. (*Biomacromolecules* 2015, 16(2):606-614) that silk fibroin heavy and light chain proteins are distinct in their rheological properties, and therefore, differential degradation rates of these constituents in PASF would imbue unpredictable changes to the viscosity of a given solution over time. Furthermore, the impact of total fibroin protein concentration on viscosity is non-linear, also shown by Zafar et al., and escalates rapidly as purified fibroin solutions exceed 100 mg/mL, thus restricting the useable concentration of the protein solution for a particular application.

To determine whether these limitations could be overcome through amino acid transformations that culminate in SDP, 80-100 mL of PASF or autoclave-treated SDP were generated at 50-80 mg/mL. To assess the impact of heating PASF to a level below autoclaving conditions, PASF was heated to 225° F. for 30 minutes in a jacketed reaction vessel as described above. Purified solutions were placed in 140 mm shallow plastic weigh boats in a laminar flow hood (Baker Sterilgard 56400, Class II) at ~22° C. to facilitate evaporation. At periodic intervals, concentrating samples were collected to measure protein content (calculated in % w/w) and assess viscosity using a viscometer (Brookfield LVDV-E, spindle 00). Measurements were made at spindle revolutions per minute (about 1-100 rpm) that permitted a torque range that would permit accurate viscosity measurements, measured at 25° C., on 16 mL sample volumes.

As summarized in FIG. 5, the viscosity of PASF rose precipitously when solutions exceeded 75 mg/g. Furthermore, PASF could not be concentrated to >200 mg/g, at which point fibroin protein began to become insoluble. PASF solutions heated to 225° F. prior to dialysis demonstrated the impact of heat on solution viscosity. In particular, heated PASF exhibited decreased viscosities at any given concentration relative to non-heated PASF. In contrast, SDP exhibited minimal changes in solution viscosity at concentrations at or below 140 mg/g (FIG. 5). Furthermore, SDP viscosity remained below ~10 cP at protein concentrations where PASF could no longer stay in solution (e.g., at 240 mg/g). Importantly, SDP was capable of remaining homogeneous at concentrations exceeding 400 mg/g, where viscosities stayed below 150 cP.

An aqueous solution of SDP thus exhibits lower viscosity when compared to PASF at all concentrations above 4% w/w. Additionally, gelation begins to occur at about 20% w/w for the PASF solution at which point accurate viscosity measurements where not possible, while the SDP material increased in concentration without exhibiting gelation, aggregating behavior, or significant increases in viscosity through 25% w/w solutions.

Taken together, these results clearly demonstrate that the process-related protein transformations described herein for the preparation of SDP are needed for the production of a highly concentrated, low viscosity protein solution.

Example 5. Formation of Pyruvoyl Peptides

The chemical reaction illustrated in Scheme 1 described above results in the production of a pyruvoyl peptide. The pyruvoyl peptide degrades into pyruvate, which is readily detectable by a standard pyruvate assay. To demonstrate that the application of heat and pressure (e.g., the environment in an autoclave) could facilitate pyruvoyl generation in silk fibroin protein processing, aqueous silk fibroin solution (5% w/v in water) was produced using the prior art method described above. The material was then heated in a thermally jacketed beaker (ChemGlass, NJ) at defined temperatures up to 210° F., or just below the boiling point of the protein solution. Specifically, Prior Art Silk Fibroin protein solutions were heated to ~65° C. (~150° F.), ~90° C. (~200° F.), or ~99° C. (~210° F.), and then sampled upon reaching these temperatures to measure pyruvate concentrations via colorimetric assay (Pyruvate Assay Kit, MAK071, Sigma-Aldrich).

The production of pyruvate increased in both 90° C. and 99° C. heated samples. Pyruvate increased by 50% at 99° C. (FIG. 6A). To determine whether pyruvate conversion was further enhanced over time, the samples were heated to 99° C. and maintained at this temperature for 30 minutes (FIG. 6B). Sustained heating caused a robust increase in pyruvate formation, generating more than a fourfold increase in pyruvate relative to non-heated samples. These results indicate that upon heating the silk fibroin protein, there is a chemical conversion to pyruvoyl containing material as detected by pyruvate assay. From this data it can be concluded that within a more extreme heating environment, such as in an autoclave process, the silk fibroin protein will be stimulated to produce pyruvate to an even greater extent. This provides further evidence that the final SDP product is a chemically distinct entity from the Prior Art Silk Fibroin.

Example 6. Amino Acid Profile Analysis

The impact of heating silk fibroin fibers dissolved in 9.3M LiBr solution on amino acid profile was investigated using ion-exchange chromatography (AOAC Official Method 994.12, Amino Acids.com, MN). Samples were produced using the processes described in Example 1 for both the SDP Solution and the Prior Art Silk Fibroin Solution. The solutions were then submitted in like-concentrations for evaluation by chromatography. Particular attention was paid to the amino acids serine, glycine, and alanine, given their prominent constitution in the silk fibroin protein primary sequence and their key roles in secondary structure formation.

SDP solution samples were found to contain 40% less serine relative to Prior Art Silk Fibroin Solution samples (FIG. 7A), and a corresponding increase in the levels of glycine and alanine (FIG. 7B). These results indicate a significant change in amino acid content, which changes result in different (and enhanced) chemical and physical properties as a result of the autoclave process. These results also corroborate with findings in the literature by Mayen et al. (*Biophysical Chemistry* 2015. 197:10-17) where increased serine content was shown to increase initial aggregation of silk fibroin proteins, while silk fibroin protein with increasing glycine and alanine content required greater energy thresholds to initially aggregate. Therefore, by reducing serine and increasing both alanine and glycine content, the propensity (and/or possibility) for aggregation is reduced or eliminated, leading to the greater solution stability of SDP.

Example 7. Artificial Tear Formulations

The SDP solution was used to formulate an artificial tear for use in treating ophthalmic conditions and disorders. The artificial tears can be specifically formulated and used for the treatment of the disorder 'dry eye'. The artificial tears can also be formulated and used for treatment of an ocular wound created by either accidental or surgical insult.

Incorporation of SDP into artificial tear formulations is especially advantageous because it increases the spreadability of the formulation. SDP-containing artificial tears also have an extremely long shelf-life due to their solution stability. The block co-polymer arrangement of hydrophilic and hydrophobic amino acid groups located in the backbone of the SDP protein allows the molecules to interact with both water-soluble and water-insoluble chemistries within the tear film. When included as an ingredient in an artificial tear eye drop formulation, the SDP ingredient acts to enhance the spreadability of the artificial tear, which provides additional comfort to the patient and prolonged efficacy to the product. The aggregating groups of prior art silk fibroin solution are not required to enable this spreading property, so it is advantageous to remove these regions to enhance protein product stability in solution over time.

The enhanced spreading ability of the artificial tear was demonstrated by comparing leading brand artificial tear products with an artificial tear formulated using the SDP ingredient. A test protocol was used to evaluate the effect of mechanical spreading on the wetting ability of various eye drop products. Phosphate buffered saline (PBS), TheraTears® (TT) artificial tears by AVR, Blink® Tears eye drops by AMO, Systane Balance® (SB) eye drops by Alcon, and a formulation containing SDP were compared in the experiment. For reference, PBS contained 100 mmol PBS salts in water, TT contains 0.25% wt. carboxymethyl cellulose (CMC) as the active ingredient with additional buffering salts in water, Blink contains 0.2% wt. hyaluronic acid (HA) as the active ingredient with buffering salts in water, SB contains 0.6% wt. propylene glycol (PG) as the active ingredient with HP-guar and mineral oil as enhancing excipients with buffering salts, and the SDP solution contained 0.25% wt. CMC with 1% wt./vol. SDP and buffering salts (i.e., 0.01M phosphate buffer containing 137 mM NaCl).

Figure 8:
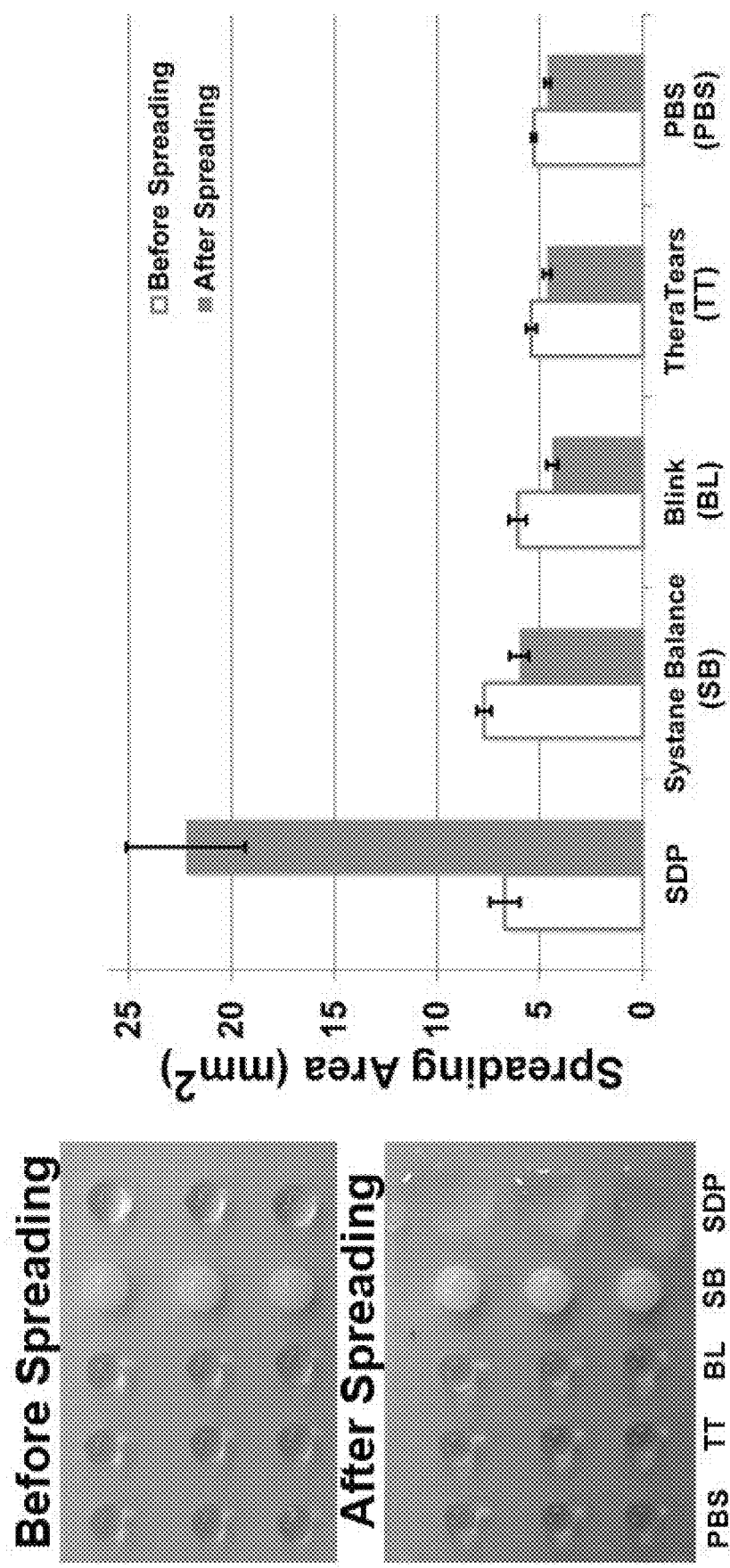
FIG. 8. Various sample formulations were placed on a hydrophobic wax surface: phosphate buffered saline (PBS), TheraTears (TT), Blink, Systane Balance (SB), and a 5% w/v SDP formulation (shown on the left side of the figure). Formulation solution spreading was imaged, and the spreading area was then measured at time points before and after mechanical spreading (data shown on the right side of the figure). After mechanical spreading, the SDP formulation showed significantly enhanced spreading (by over threefold) compared to all other sample formulations.

This group of compared products included multiple demulcents and additional active ingredient-enhancing excipients. FIG. 8 shows that inclusion of the SDP ingredient enhances mechanical spreading ability by nearly four-fold over the leading brand formulations. This post-spreading enhancement can be compared to the eyelid wiping across the ocular surface. Thus, the SDP ingredient allows for better comfort to the patient while enhancing efficacy and stability of the product. Furthermore, the addition of SDP over prior art silk fibroin solution as an ingredient is advantageous because the prior art silk fibroin solution would gel and aggregate during the product shelf life. These aggregates would be unacceptable in an ophthalmic formulation based on current United States Pharmacopeia (USP) requirements (Particulate Matter in Injections: USP <788-789>).

Example 8. Analysis of Protein Secondary Structure

The impact of autoclave processing on secondary structure formation was assessed. A 5% w/v SDP Solution and a 5% w/v Prior Art Silk Fibroin Solution (100 µL each) were cast on 14 mm diameter silicone rubber surfaces (n=6) and allowed to air dry into solid films over several hours. The films were then assessed by ATR-FTIR (Nicolet iS10, Thermo Scientific, MA) at a 4 nm resolution of 16 scans each.

Figure 9:
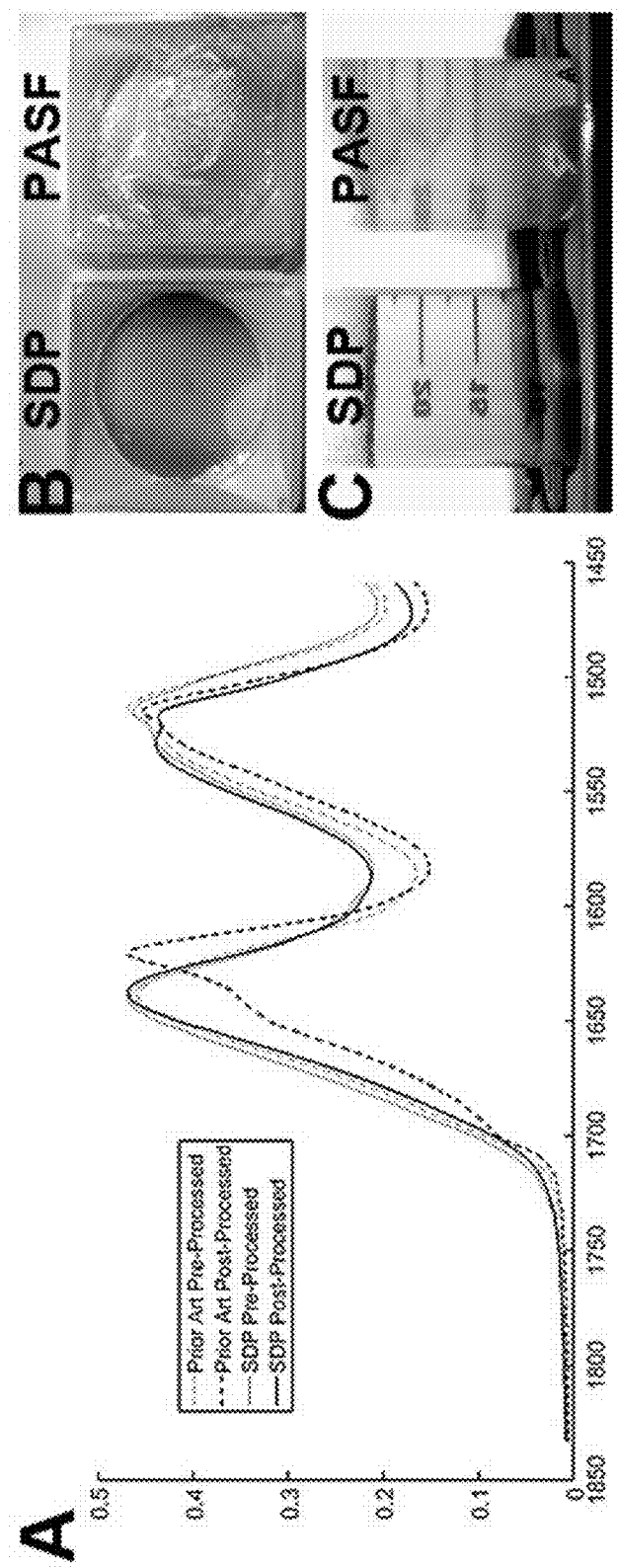
FIG. 9A-C. Amino acid transformation in SDP impairs secondary protein structures and permits dissolution. (A) FTIR spectra of both pre-processed and post-processed water-annealed samples of PASF Solution and SDP Solution. The prior art samples show significant beta-sheet signature peaks post water-annealing around 1624 $cm^{-1}$ and 1510 $cm^{-1}$, while the spectrum of the SDP solution does not indicate formation of beta-sheet peaks and instead indicates significantly reduced beta-sheet content post-processing. (B) Representative images of SDP and PASF silk solutions desiccated to form films. (C) Subsequent dissolution of SDP films in water was complete, indicating that no beta-sheet secondary structures had formed; however, PASF films were unable to dissolve entirely, rendering a mixture of partially dissolved PASF and undissolved beta-sheet-containing protein aggregates.

The films were also processed for 5 hours within a water-annealing chamber, which is a vacuum container with water filled in the basin to create a 100% RH environment. The water vapor induces secondary structure formation of fibroin protein films, most notably beta sheet structures as shown by Jin et al. (*Advanced Functional Materials* 2005, 15:1241-1247). The film samples were then reanalyzed with the FTIR as described above. Spectral analysis revealed that SDP and Prior Art Silk Fibroin films produced similar IR signatures before material processing, but the SDP material lacked the ability to form beta sheet secondary structures post-processing as noted by the absence of well-known beta sheet absorption peaks in the Amide I and II regions of the IR spectrum at 1624 cm$^{-1}$ and 1510 cm$^{-1}$, respectively (FIG. 9A). This finding represents a significant difference in material composition of the two samples, which is a direct indication that the amino acid chemistry is inherently different in the SDP and PASF samples.

To represent the impact of secondary structure functionally, 150 mL samples of the solutions were both dried within a convective clean air environment at room temperature for 48 hours. This resulted in the formation of solid protein material that demonstrated significant differences in appearance between the two solutions (FIG. 9B). Most notably, the autoclave-processed SDP material demonstrated a darker yellow translucency that indicates chemical changes to aromatic amino acids, when compared to the transparent and more pellucid PASF material. In addition, the SDP material formed a dried skin that prevented the lower region of the volume from completely dehydrating and thus partially remained liquid. This was not the case for the Prior Art Silk Fibroin material, which was completely dried and physically distorted into a wavy material. These results indicate significant changes to the material's mechanical properties, and thus chemical interactions, as a result of the autoclave processing to form the SDP material.

To assess solubility as a function of the autoclave processing, samples of both dried materials were weighed and reconstituted in deionized water (diH$_2$O). For the SDP material the tough outer skin later was peeled off and weighed, while for the Prior Art Silk Fibroin a portion of the material was broken off and weighed. For both samples, 500 mg of material was added to 25 mL of diH$_2$O (2% w/v solution) and then vortexed at high-speed setting for 10 minutes. Interestingly, the SDP material completely dissolved in the diH$_2$O volume, while the Prior Art Silk Fibroin material dissolved only very minimally (FIG. 9C). These results indicate the material solubility and solubility chemistry was distinctly changed between the SDP and Prior Art Silk Fibroin materials due to the autoclave processing.

Example 9. Impact of Enzymatic Fibroin Cleavage on Solution Stability

To identify whether the increased stability of SDP is a direct consequence of amino acid transformation or merely due to the production of smaller fibroin proteins generated by hydrolysis, Prior Art Silk Fibroin (PASF) was treated with the serine protease trypsin to enzymatically break down fibroin as has been performed by Shaw (Biochem. J. 1964, 93(1), 45-54). In brief, 0.5-1.0 mg/mL of trypsin isolated from bovine pancreas (Sigma-Aldrich, T1426, MO) was added to PASF (78 mg/mL) solution containing HEPES buffer salts, mixed, and then incubated at 37° ° C. for 1, 2, 4, or 6 hours. Reactions were stopped with the addition of 2 mM phenylmethylsulfonyl fluoride (PMSF), and the extent of fibroin fractionation was measured by 1D-PAGE and densitometry as described in Example 3.

TABLE 1

Average molecular weight of prior art silk fibroin enzymatically cleaved with trypsin over increasing durations.

| Treatment | Average Molecular Weight (kDa) |
|---|---|
| PASF (Control) | 107 |
| 1 hour trypsin | 93 |
| 2 hour trypsin | 79 |
| 4 hour trypsin | 70 |
| 6 hour trypsin | 70 |

Figure 10:
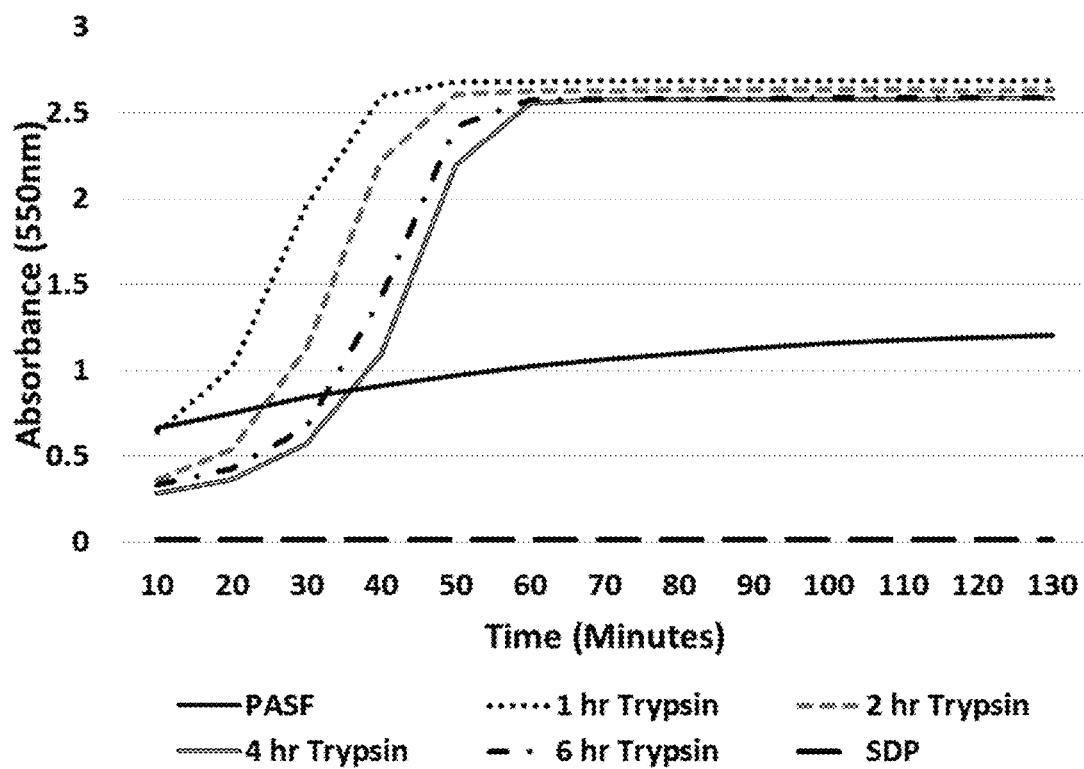
FIG. 10. Enzymatic cleavage of silk fibroin with trypsin enhances instability and accelerates gel formation but does not affect SDP. Summary graph depicting absorbance (550 nm) of ultrasonicated PASF previously treated with trypsin for indicated time points. Increasing absorbance indicates fibroin beta-sheet formation which culminates in gel formation, demonstrating solution instability.

As shown in Table 1, trypsin treatment proved effective to progressively reduce the average molecular weight of PASF until 4 hours. These materials were then subjected to ultra-sonication to initiate beta-sheet formation and gelation as performed and described by Wang et al. (*Biomaterials* 2008. 29(8): 1054-1064). The fractionation of PASF with trypsin caused a dramatic acceleration in the kinetics of gelation, however, which is summarized in FIG. 10. Specifically, 1 hour trypsin treatment of PASF induced gel formation by ~40 minutes following sonication, which was slowed to ~60 minutes in PASF exposed to trypsin for 4 hours. Control PASF (in the presence of deactivated trypsin) exhibited increasing instability with time which reached maximal beta-sheet formation (indicated by absorbance at 550 nm, FIG. 10) by approximately 1300 minutes (data not shown). In contrast, silk-derived proteins (SDP) showed no tendency toward instability during this time frame, evidenced by a minimal and unchanging absorbance at 550 nm (FIG. 10). These results indicate that fractionation of PASF by enzymatic cleavage of select peptide bonds, without amino acid transformation, are ineffective and in fact counter-productive to forestall beta-sheet formation, instability, and gel formation.

Example 10. Impact of Disulfide Bonds on Fibroin Stability

Figure 11:
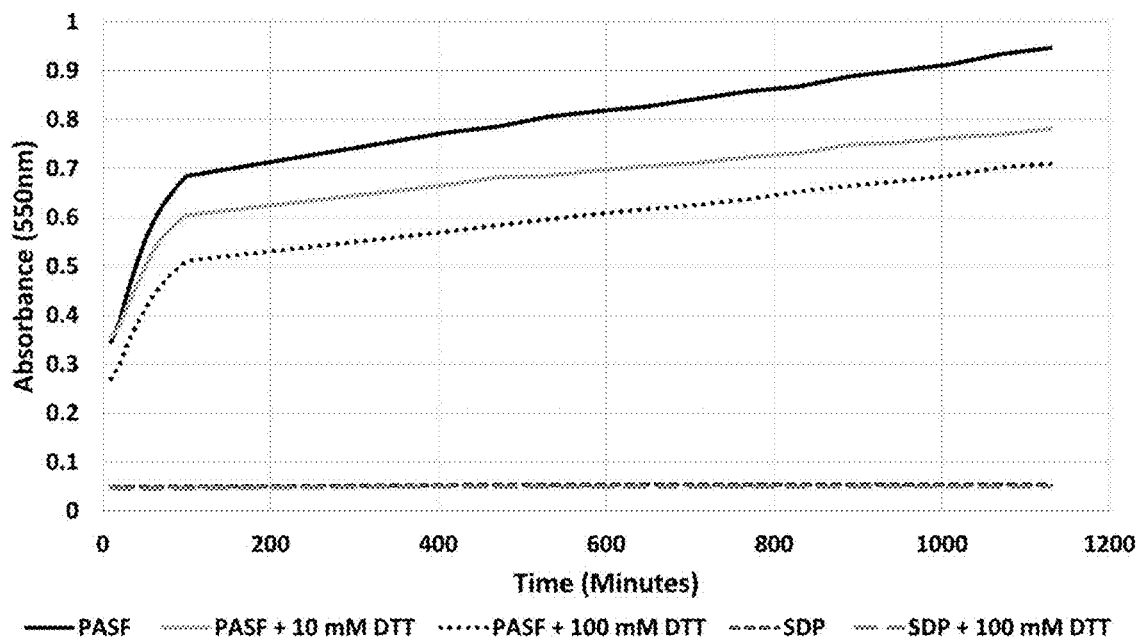
FIG. 11. Summary graph depicting longitudinal optical absorbance (550 nm) of PASF solutions treated with 0 (control), 10, or 100 mM dithiothreitol (DTT) 30 minutes prior to ultrasonication. The data provides an indicator of secondary structure formation in PASF or SDP solutions over time. Accumulating beta-sheet formation, shown as an increasing absorbance, occurs immediately after sonication of PASF solutions (e.g., within 30 minutes and subsequently increasing). Conversely, SDP exhibits no tendency towards secondary structure formation. Reduction of disulfide bridges with DTT retards beta-sheet and subsequent gel formation compared to control PASF, but the material ultimately forms significant amounts of beta-sheets. In contrast, SDP showed no tendency to form secondary structures and remained stable. Thus, reduction of disulfide bridges in native fibroin improves stability but does not prevent gel formation, and longitudinal instability of PASF is abolished in SDP.

The association between the fibroin heavy and light chain dimers exists through a single covalent disulfide bond, as elucidated by Tanaka et al. (*Biochim Biophys Acta.* 1999, 1432(1):92-103). Dimer separation can instigate fibroin peptide-peptide interactions, which culminate in insoluble protein aggregation (Shulha et al., *Polymer* 2006, 47:5821-5830) that precedes beta-sheet formation and gelation (Nagarkar et al., *Phys. Chem. Chem. Phys.* 2010, 12:3834-3844). Therefore, to determine whether disruption of the fibroin heavy-light chain dimer stimulates protein aggregation and therefore instability, PASF was treated with the disulfide bond reducing agent dithiothreitol (DTT, Sigma-Aldrich, MO) at 0 (control), 10, or 100 mM, and was then subjected to ultrasonication to instigate beta-sheet and gel formation. As shown in FIG. 11, the reduction of the disulfide bond in PASF with 10 mM DTT decelerated, but did not inhibit instability, indicated by increasing 550 nm absorbance over time relative to control samples. These effects were further pronounced with 100 mM DTT, but still ineffective at forestalling instability. In contrast, SDP exhibited no tendency toward instability following ultrasonication, indicated by an unchanging baseline absorbance, which was unaffected by the addition of DTT (FIG. 11). Collectively, these results demonstrate that the fibroin disulfide bridge participates in the mechanisms underlying PASF instability, but their reduction is ineffective to prohibit beta-sheet formation and gelation.

Example 11. Fibroin Stability Requires Heat in the Presence of Lithium Bromide To determine whether the heat-mediated transformation of amino acids in PASF requires lithium bromide, studies were undertaken to identify if similar stability could be achieved when PASF was heated in the final aqueous solution (lacking lithium bromide). To this end, PASF was prepared (without additional heating) at 50 mg/mL concentration and then heated in a jacketed reaction beaker (Chemglass, CG-1103-01, NJ) connected to a heater/chiller (Neslab, RTE-7, ThermoScientific, MA) actively circulating silicone oil heat exchange fluid (AceGlass, 14115-05, NJ). The circulator was set to ~200° F., the temperature just below the boiling point of PASF lacking lithium bromide salts, and was allowed to stabilize for 15±1 minutes. PASF (25 mL) was incubated in the reaction beaker with a PTFE-coated stir bar and placed on a stir plate (IKA C-MAG HS7, NC) to ensure solution temperature homogeneity. PASF temperature was actively monitored throughout the heating period using an external thermocouple (Omega HH-603, Omega Engineering, CT), and samples (3 mL) were removed at the following timepoints:

| Temperature | Timepoint |
| --- | --- |
| 68° F. | 0 min |
| 196 ± 1° F. | 30 min |
| 196 ± 1° F. | 60 min |
| 196 ± 1° F. | 90 min |
| 196 ± 1° F. | 120 min |

Figure 12:
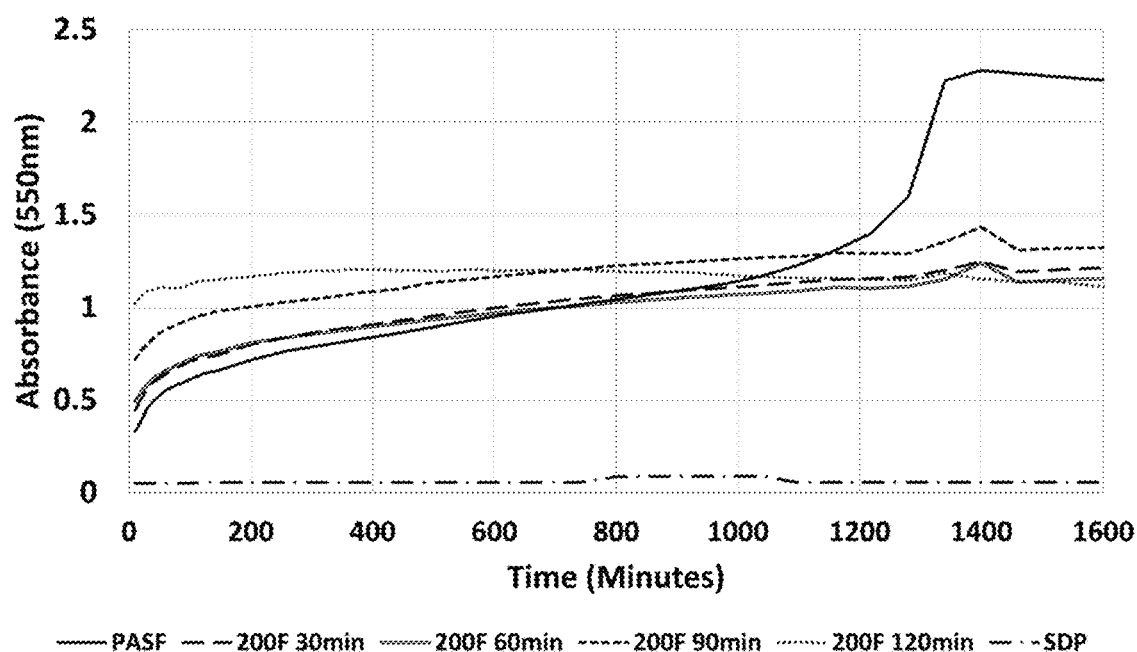
FIG. 12. Heating PASF in the absence of lithium bromide (LiBr) impairs gelation. Summary graph depicting optical absorbance (550 nm) from PASF solutions not heated (control) or heated at ~200° F. for indicated durations prior to ultrasonication. Solution heating caused an increase in basal absorbance which increased with heating duration relative to non-heated PASF. All PASF solutions demonstrated an increase in absorbance over time, indicating change in protein properties. In contrast, SDP exhibited no change in absorbance following ultrasonication throughout the duration of the experiment.

Drawn samples were then subjected to ultrasonication to instigate beta-sheet formation and gelation, as has been described previously by Wang et al. (*Biomaterials* 2008, 29(8): 1054-1064). To compare these results with PASF that had been heated in the presence of lithium bromide, SDP was also ultrasonicated separately, and absorbance at 550 nm monitored longitudinally to compare the kinetics of fibroin instability. As shown in FIG. 12, the application of heat to PASF actually increased baseline absorbance and hence instability relative to non-heated control samples. Furthermore, the duration of heat exposure (from 30 to 120 minutes) to PASF was inversely proportional to basal absorbance, indicating that the presence of lithium bromide during production of SDP is needed to achieve the minimal absorbance observed in this latter solution (FIG. 12). Furthermore, 550 nm absorbance continued to escalate in all of the heated PASF solutions over time but did not change from baseline in ultrasonicated SDP solutions, thus clearly demonstrating that heat-treated samples were undergoing beta-sheet formation and therefore becoming unstable. Collectively, these results indicate that heat mediated hydrolysis of PASF in the absence of lithium bromide is insufficient to mediate the amino acid transformations that facilitate protein stability to the same degree as for the SDP described herein.

While specific embodiments have been described above with reference to the disclosed embodiments and examples, such embodiments are only illustrative and do not limit the scope of the invention. Changes and modifications can be made in accordance with ordinary skill in the art without departing from the invention in its broader aspects as defined in the following claims.

All publications, patents, and patent documents cited herein are incorporated by reference herein, as though individually incorporated by reference. No limitations inconsistent with this disclosure are to be understood therefrom. The invention has been described with reference to various specific and preferred embodiments and techniques. However, it should be understood that many variations and modifications may be made while remaining within the spirit and scope of the invention.

What is claimed is:

1. A fibroin-derived protein composition prepared by a process comprising heating an aqueous fibroin solution at an elevated pressure, wherein:

the aqueous fibroin solution comprises lithium bromide at a concentration of at least about 8M, and the aqueous fibroin solution is heated to at least about 105° C. (221° F.) under a pressure of about 10 PSI to about 20 PSI for at least about 20 minutes in the presence of the lithium bromide;

to provide a protein composition comprising fibroin-derived protein wherein:

the primary amino acid sequences of the fibroin-derived protein composition differ from native fibroin by at least 6% with respect to the combined amino acid content of serine, glycine, and alanine, based on the combined absolute values of the differences in the content of serine, glycine, and alanine;

cysteine disulfide bonds between the fibroin heavy and fibroin light protein chains of fibroin are reduced or eliminated;

the protein composition has a serine content that is reduced by greater than 25% compared to native fibroin protein, wherein the protein composition comprises between 4.5% and 7.5% serine amino acids residues;

wherein the average molecular weight of the fibroin-derived protein composition is less than about 100 kDa; and wherein the protein composition has an aqueous viscosity of less than 5 cP as a 10% w/w solution in water.

2. The protein composition of claim 1 wherein the aqueous fibroin solution is heated to a temperature of about 115° C. (239° F.) to about 125° C. (257° F.) under a pressure of about 15 PSI to about 20 PSI for at least about 30 minutes.

3. The protein composition of claim 1 wherein the fibroin-derived protein has an average molecular weight of less than about 60 kDa.

4. The protein composition of claim 1 wherein the protein composition has an aqueous viscosity of less than 10 cP as a 24% w/w solution in water.

5. The protein composition of claim 1 wherein a primary amino acid sequences of the fibroin-derived protein differ from native fibroin by at least 8% with respect to the combined amino acid content of serine, glycine, and alanine based on a combined absolute values of the differences in the content of serine, glycine, and alanine.

6. The protein composition of claim 1 wherein the fibroin-derived protein comprises greater than 46.5% glycine amino acids.

7. The protein composition of claim 6 wherein the fibroin-derived protein comprises greater than 48% glycine amino acids.

8. The protein composition of claim 1 wherein the fibroin-derived protein comprises greater than 30% alanine amino acids.

9. The protein composition of claim 8 wherein the fibroin-derived protein comprises greater than 31.5% alanine amino acids.

* * * * *